United States Patent [19]

Daneshvar

[11] Patent Number: 5,383,893
[45] Date of Patent: Jan. 24, 1995

[54] DEVICE FOR PREVENTING POST-CATHERIZATION WOUND BLEEDING

[76] Inventor: Yousef Daneshvar, 21459 Woodfarm, Northville, Mich. 48167

[21] Appl. No.: 42,560

[22] Filed: Apr. 5, 1993

Related U.S. Application Data

[63] Continuation-in-part of Ser. No. 989,825, Dec. 14, 1992, which is a continuation-in-part of Ser. No. 800,085, Nov. 29, 1991, Pat. No. 5,263,966.

[51] Int. Cl.⁶ .................................................. A61B 17/12
[52] U.S. Cl. ........................................ 606/201; 606/202; 602/62; 602/67; 128/118.1; 128/96.1
[58] Field of Search ............... 606/112, 201–204; 128/118.1, 98.1; 602/13, 67, 62; 128/96.1

[56] References Cited

U.S. PATENT DOCUMENTS

| | | | |
|---|---|---|---|
| 976,550 | 11/1910 | Coddington | 602/67 X |
| 2,493,406 | 1/1950 | Hicks | 128/118.1 X |
| 3,171,410 | 3/1965 | Towle et al. | 128/118.1 X |
| 4,135,503 | 1/1979 | Romano | 128/118.1 X |
| 4,622,957 | 11/1986 | Curlee | 128/118.1 |
| 4,957,105 | 9/1990 | Furth | 128/96.1 |
| 4,977,893 | 12/1990 | Hunt | 128/96.1 X |
| 5,170,781 | 12/1992 | Loomis | 128/118.1 |

FOREIGN PATENT DOCUMENTS

| | | | |
|---|---|---|---|
| 910340 | 6/1946 | France | 128/118.1 |
| 821824 | 11/1951 | Germany | 128/118.1 |
| 45062 | 7/1908 | Switzerland | 128/118.1 |
| 4383 | of 1880 | United Kingdom | 128/118.1 |
| 462426 | 5/1937 | United Kingdom | 602/67 |
| 9011744 | 10/1990 | WIPO | 606/202 |

Primary Examiner—Michael H. Thaler

[57] ABSTRACT

The devices have various features including balloons that are joined by a line of folding parallel with the groin line and a wrap for holding the balloons that has a similar line of folding, but is unconstrained between abdomen- and thigh-wrap portions so as to allow the person to sit up and lie down while balloon pressure is maintained on the groin. Another feature is a stretchable layer of wrap that includes zig-zag elements that allow limited stretch and then prevent further stretch. Rigid covers can be used over the balloons. The balloons are also used with shorts that can be worn by the person.

2 Claims, 19 Drawing Sheets

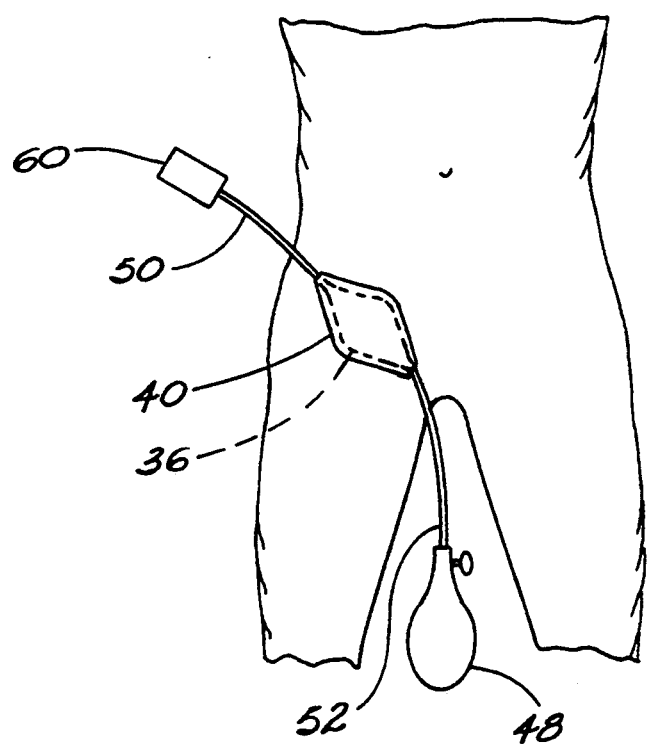
*Fig. 5*
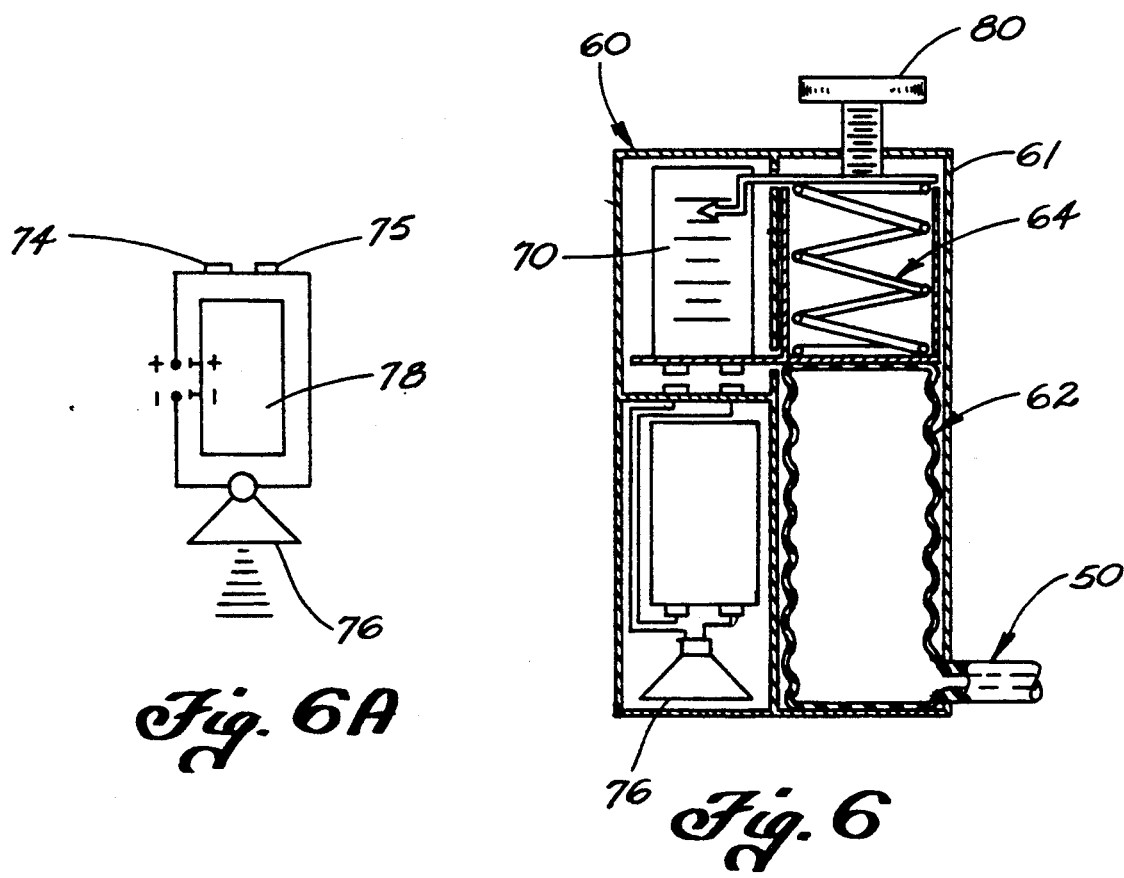
*Fig. 6A*
*Fig. 6*

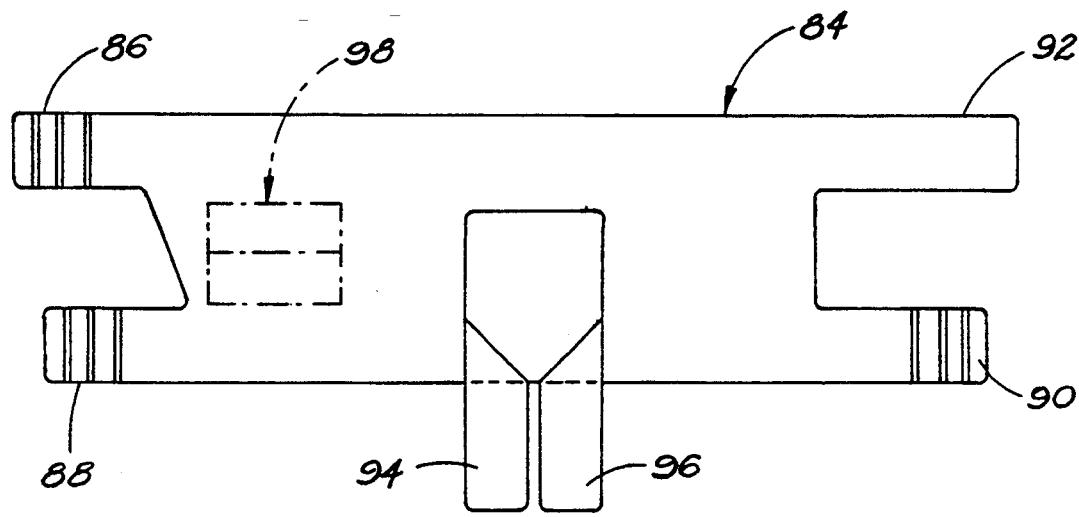
Fig. 7
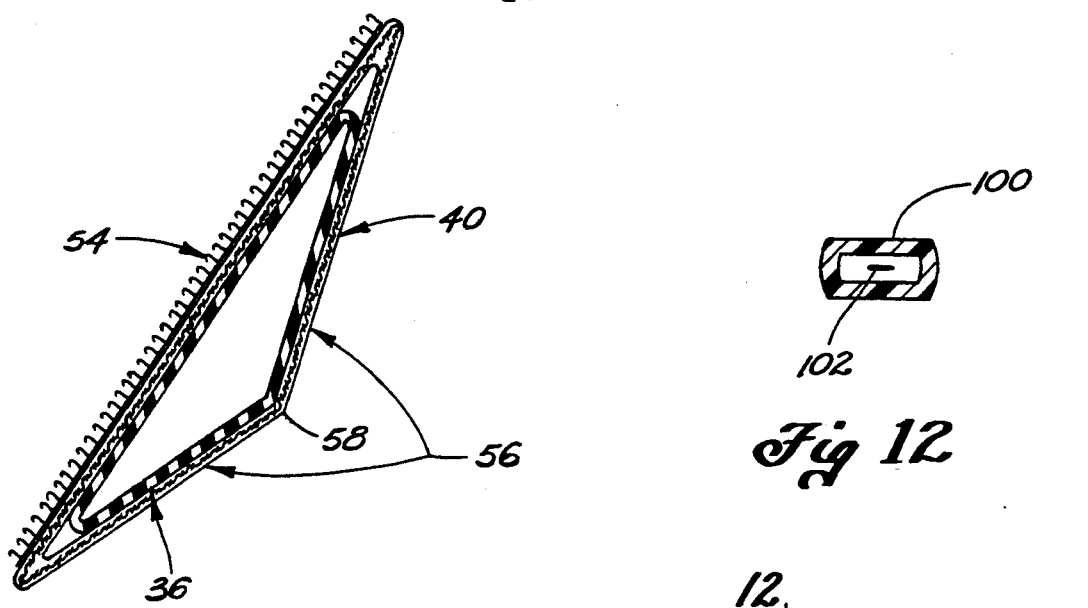
Fig. 8
Fig. 12
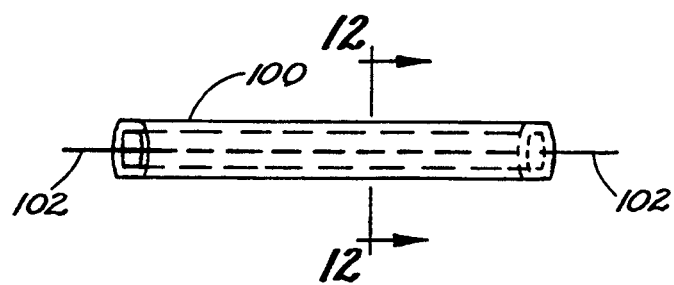
Fig. 11

DEVICE FOR PREVENTING POST-CATHETERIZATION WOUND BLEEDING

REFERENCE TO RELATED APPLICATIONS

This application is a continuation-in-part of pending application Ser. No. 07/989,825 filed Dec. 14, 1992, which is a continuation-in-part of pending application Ser. No. 07/800,085 filed Nov. 29, 1991, now U.S. Pat. No. 5,263,966.

FIELD OF THE INVENTION

This invention relates to the post-catheterization prevention of bleeding from a wound created as a consequence of inserting a catheter, or other similar device, into a vessel. More particularly, it relates to preventing bleeding from a wound proximate a person's groin.

BACKGROUND AND SUMMARY OF THE INVENTION

One of the common concerns in cardiac catheterization and related interventions is the problem of bleeding after catheterization of a vessel. This well known and familiar problem may even need corrective surgery in extreme cases.

A commonly used method of preventing such complication is quite primitive, and may be ineffective in some instances. That method is to position a sand bag in the area over a pressure bandage. In general, it may be considered a rather crude and uncomfortable method since, 1) it does not apply an appropriate amount of pressure all the time, 2) the sand bag may slide and/or fall, 3) the patient must be kept practically motionless to avoid dislocation of the sand bag, and 4) the patient is usually told not to raise the head over 15 degrees. Insofar as the applicant is aware, no other method has replaced the sand bag to any significant degree.

This problem has led to the applicant's creation of a much better alternative, which the applicant has named the D. Device. This device affords much easier use, gives much better pressure control, and is more comfortable for the patient. Not only can the patient move more, but it is believed that he/she may be discharged earlier from the hospital.

Briefly, the device is designed to prevent bleeding after catheterization of a groin vessel in connection with any of a number of different interventions, such as angiography for the heart, brain, arteries, etc., during which a vessel, such as an artery, has to be entered for diagnostic or treatment purposes. Naturally, the resulting wound has tendency to bleed.

The device comprises a main wrap, made preferably from tough synthetic fabric, which wraps around both the lower abdomen and the upper thighs to give support for the application of pressure to the groin by a specially shaped inflatable balloon contained within the wrap. The pressure inside the balloon can be monitored by a gauge, which can also have a safety alarm to indicate if the pressure inside the balloon drops. Another wrap, made preferably from a thin layer of non-irritating, soft, disposable material matching the shape of the main wrap may cover the skin under the main wrap to prevent contamination. Means are also provided so that bleeding which may occur after the device has been placed on the person can be seen by an observer.

Lately I have noticed that the anxiety of patients from bleeding after catheterization is real and well founded; they get very concerned about the development of bleeding and even minimal expansion in their arteries. I have heard from my own patients about their fear that with movement, their artery may open and bleed. These reactions, as well as worries of people with hernia, made me believe that there is a need for better protection and assurance of patients from bleeding and complications after cardiac catheterization and related interventions. This thought, as well as my own concern about patients' well being, have resulted in a modification and improvement in my previous device. This improvement, which I call D.Device 2, will be used to protect a patient when he or she is ready to be discharged from the hospital or cardiac catheterization lab clinic. It also provides peace of mind to patients, their relatives, and the physician. Also, the anxiety and concern of patients with hernia have resulted in modification of this unit to allow it to be very beneficial in patients with hernia or similar problems.

D.Device 2 comprises a unit that has a pressurized balloon that is held in place by straps, wraps, or shorts, to prevent bleeding and related complications in the groin area after cardiac catheterization or similar procedures. The unit is also very beneficial in patients with hernia or similar problems by applying pressure in front of a hernia to prevent its expansion related problems.

This unit comprises one or two balloons, each having a shape similar, but not identical, to a half moon. These balloons, or their covers, have lines, areas or patches of adhesive film or Velcro TM on the surface that allow their position to be modified and adjusted for best placement in the beginning and later as many times as necessary. These balloons are held in place by use of a support system that consists of straps, wraps, or special shorts that allow the pressure to be built up and kept in the groin area for prevention of bleeding.

The use of two balloons, as well as special shapes of the support systems, gives a great advantage over my previous models by allowing a patient to bend his or her leg easily and to sit in a chair, which is going to occur most of the time during transportation by car, etc. The unit may also have another balloon to go over these two balloons and make delivery of a greater pressure in the area possible when the patient lays on the bed. This unit will provide the protection to the area after cardiac catheterization and related procedures, and I believe will give a great deal of peace of mind to the patients and will make their anxiety disappear. A newer means for finding bleeding after catheterization in the area is also mentioned, involving use of an electric system connected to an alarm system.

In my further improvement invention, which I call D.Device 3, the unit comprises an inner unit made from combinations of soft absorbent layer such as a cotton fabric and an elastic, stretchable, non-irritant cover, such as a latex layer. These are connected to each other either by spots or layers of glue or by being sewed or by similar means. The outer layer of the latex will allow layers of non-stretchable material to be glued on it to cause its length to be controlled. This inner unit will be used to hold a balloon over an opening in the skin and then to allow a non-stretchable outer unit to be applied over it to hold the inner unit in place safely and allow the build up of the pressure inside the balloon. The amount of pressure will be observed by a gauge and alarm to prevent under- or over-pressurization. One other advantage of this unit is to allow the medical staff to choose different size balloons to match the size of different patients; different covers will give the same option as well, so that overall this unit will be of tremendous help in prevention of bleeding and of great help in such patients. This unit by its mere construction will provide physical and mental security to patients and allow them to feel secure and comfortable. I believe that this unit will also help these patients to be released faster and safer from the hospital after those procedures. The unit with only minimal modification can also be very useful in patients with inguinal hernia, or after hernia operations and certain surgeries.

Further detail of the invention, and other features, will be seen as the description proceeds.

BRIEF DESCRIPTION OF THE DRAWINGS

FIG. 5 is a front view showing the general application of the balloon and cover to the person's body, including an alarm associated with the balloon.

FIG. 6 is a front view of the alarm of FIG. 5 showing more detail.

FIG. 6A is a fragmentary front view of a portion of the alarm of FIG. 6 showing better detail.

FIG. 7 is a front view of an inner wrap that may also be used.

FIG. 8 is a traverse cross-sectional view in the direction of arrows 8—8 in FIG. 3.

FIG. 11 is a top view of another part that may be used.

FIG. 12 is a transverse cross-sectional view in the direction of arrows 12—12 in FIG. 11.

FIG. 30 along line 32—32 in FIG. 30.

DESCRIPTION OF THE PREFERRED EMBODIMENT

Figure 1:
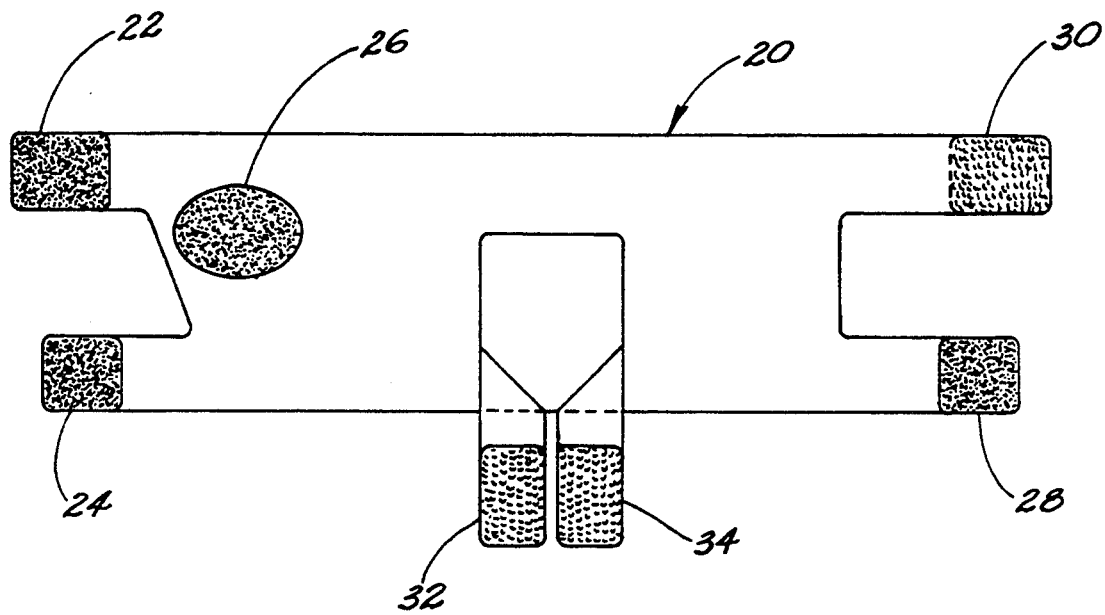
FIG. 1 is a front view of a wrap.
Figure 2:
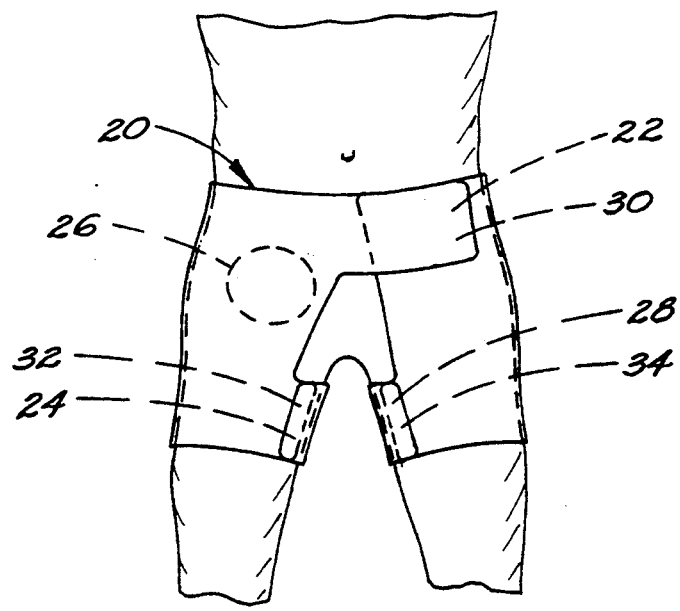
FIG. 2 is a front view showing the wrap in use on a person.

FIG. 1 shows the front view of a wrap 20 and its general appearance when opened and spread on a table. It has several areas containing Velcro TM. The soft parts 22, 24, 26, 28 of the Velcro TM are shown with straight lines, while the rough parts 30, 32, 34 are shown with dots. Parts 22, 24 are on the front face of wrap 20 as it appears in FIG. 1, and parts 30, 28 on the back face so that when wrap 20 is worn as shown in FIG. 2, the end containing soft part 22 will match and stick to part 30 to tighten the upper portion of the wrap around the lower abdomen, very much like a girdle or a belt. Part 24 will match with part 32 to wrap around the right upper thigh. Part 28 will match with part 34 to wrap around the left upper thigh. These will altogether hold the wrap tight in place.

Part 26 shown in FIG. 1 is a soft Velcro TM part and is disposed so that the back of a cover of a balloon, to be described next, will be in contact with, and stick to, it. The purpose of this part 26 is to allow adjustment of the position of the balloon and cover to the wrap in order to fit different patients. FIG. 2 gives a general idea of how wrap 20 will look when it is worn and in place on a patient's body.

Figure 3:
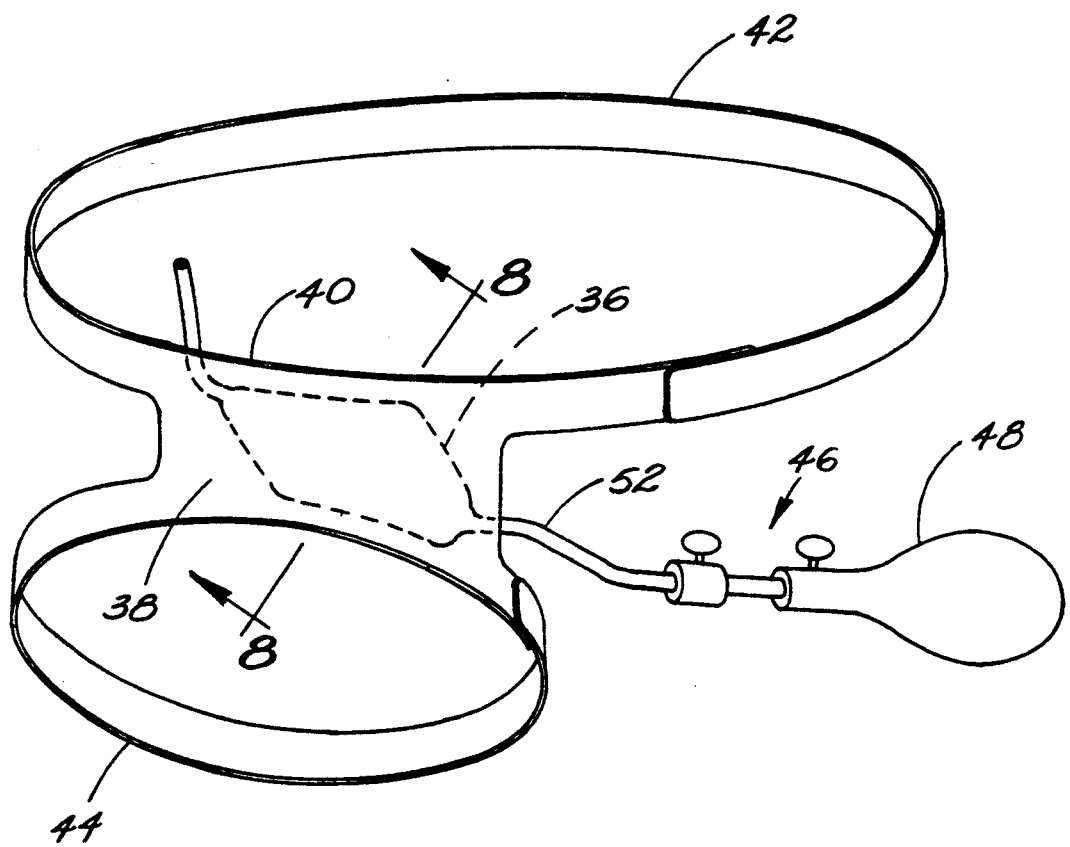
FIG. 3 is a front view of a balloon and cover.
Figure 4:
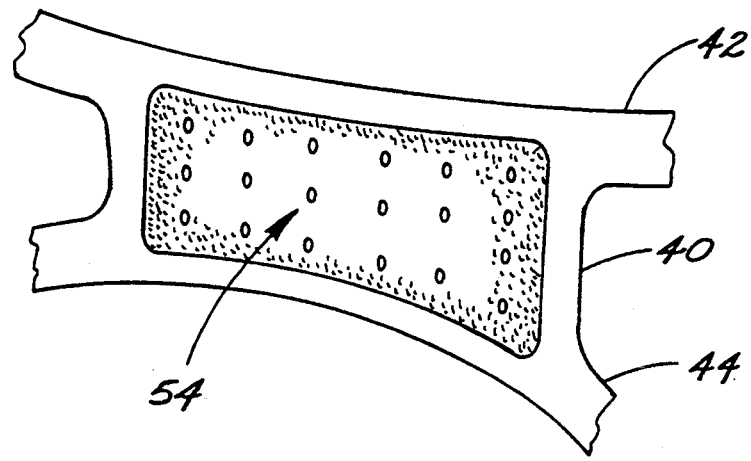
FIG. 4 is a fragmentary front view of the cover of FIG. 3 showing further detail.

FIG. 3 shows a balloon 36 inside a fabric pocket 38 of a cover 40 having straps 42, 44 extending from its corners and designed to wrap around the lower abdomen and the right thigh. The broken area in the upper strap 42 that goes around the abdomen is intended to show the disrupted piece. The lower strap 44 is to fit the upper part of the right thigh. The general appearance of balloon 36 is shown, along with its connection 46 to an inflating part 48 as well as a tube 50 to be connected to an alarm, to be described later.

Tube 50 is at one lengthwise end of balloon 36, and a further tube 52, leading to connection 46, is at the opposite lengthwise end. The two tubes 50, 52 protrude from pocket 38.

In order to best fit and adapt to the shape and anatomy of the groin area and to mainly cover the area most liable for bleeding and hematoma, balloon 36 has an almost rhomboid shape, although it may have a different shape such as a circular or sausage-type shape, such different shapes not being shown in a drawing. As seen in FIGS. 3 and 5, balloon 36 tapers toward each lengthwise end so that it is noticeably wider in the middle than at its ends. As seen in FIG. 8, balloon 36 has a flat face 54 toward wrap 20, and an opposite angled face 56 toward the groin. Face 56 has a vertex that is to be situated in the groove of the groin line and that divides face 56 into an abdomen-confronting face portion and a thigh-confronting face portion.

Cover 40 is preferably a soft non-stretchable material to resist stretching. The cover of a regular blood pressure cuff is representative of such materials. Cover 40 has two faces: one to face the area of the groin, and the other containing a rough part 54 of Velcro TM to coincide and fit the matching part 26 on wrap 20 to hold the cover and balloon in place. Cover 40 can also be attached to wrap 20 by way of a couple of snaps. The balloon and its cover can be made from transparent plastic to allow observation of possible bleeding.

Wrap 20 is made from a durable, strong, but rather soft, fabric (similar to the synthetic fabric of many handbags and soft suitcases) designed to wrap around the lower abdomen and waist area with extensions to wrap around the upper parts of the thighs. This wrapping procedure can be achieved with the use of Velcro TM shown here and/or snaps and belt-like systems or the application of shoe tie types of techniques. The idea is to hold wrap 20 rather tightly in place to stand against pressure. When wrap 20 is held tight, then its strong non-stretchable fabric material will allow application of the force over the vessels and the adjacent areas where it is needed. The balloon's shape adapts to the shape of the groin area, and it should be strong enough to hold pressures of up to 250–300 mm of mercury.

Figure 9:
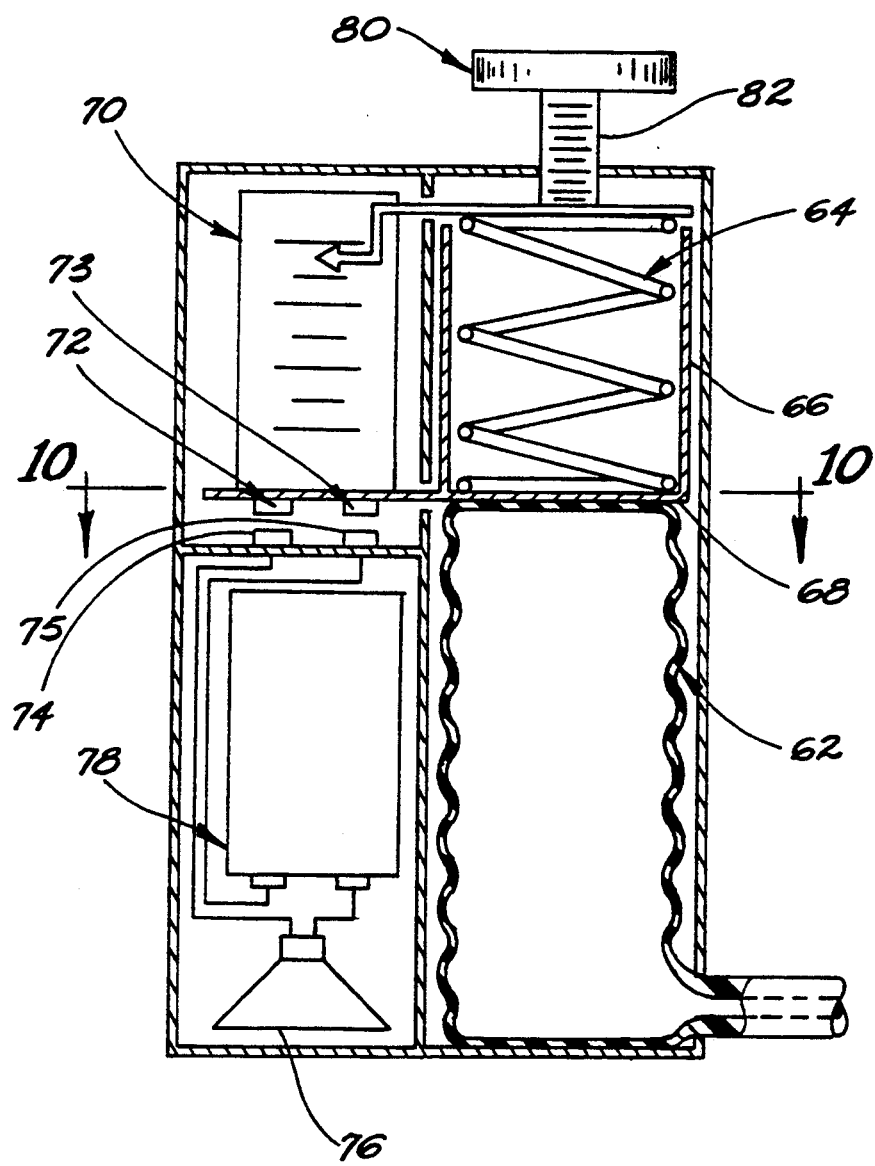
FIG. 9 is a more enlarged view of the alarm of FIG. 6.
Figure 10:
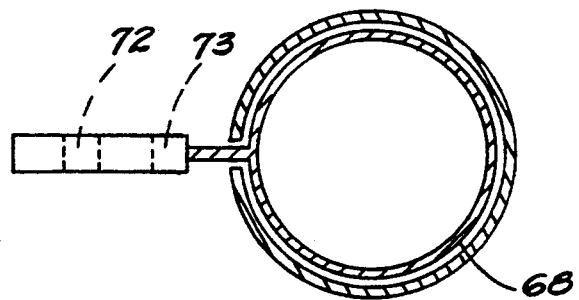
FIG. 10 is a transverse cross-sectional view in the direction of arrows 10—10 in FIG. 9.

With inflation of the balloon, the pressure will build up to be applied to the side of the vessel on the puncture side. This pressure can be monitored by connecting this part via tube 50 to the regular blood pressure monitor used in hospitals and offices or by a gauge designed for this job which is shown in FIGS. 6, 9, and 10, and which has a safety alarm part to indicate if the pressure drops. A small snap will allow the tube to be closed and the inflating device to be removed during transfers.

The alarm 60 comprises a small cylindrical box 61 having an accordion-type balloon 62 connected to balloon 36. This accordion balloon 62 will work against a circular coiled spring 64 inside box 61 and is separated by the flat, circular end plate of a cap 66 plate covering the lower end of spring 64. With a rise in the pressure inside balloon 36, this small accordion balloon 62 will be inflated, and distended and pressurized, and the pressure and distention will push cap 66 against spring 64.

Cap 66 is connected to a metal piece 68 which acts as a gauge. The gauge is to move against a scale 70 to show the relative amount of the pressure inside the balloon. If the pressure inside the balloon drops for any reason, i.e., perforation or leakage, spring 64 will push the metal piece 68 to connect its two metal terminals 72, 73 to terminals 74, 75 to complete an electric circuit and an electric buzzer 76 to sound. The circuit is powered by a battery 78. A control knob 80 comprising a screw 82 can be turned to position the top of spring 64 to adjust the level of pressure that will cause the alarm signal to sound. Turning control knob 80 also adjusts the pressure scale.

FIG. 7 shows the front view of an inner wrap 84 and its general appearance when opened and spread on a table. It is very similar to wrap 20 mentioned earlier. It is designed to be used under the outside wrap 20 to prevent contamination of the skin and the spread of dirt and germs. Wrap 84 is a layer of thin, non-irritating, soft synthetic disposable material, with a cut very similar to the wrap 20 so as to fit inside it. In order to keep wrap 84 in place when used, it has lines of gluey or sticky areas that are covered and protected by a covering plastic or paper that will be removed to expose the gluey areas at the time of use. The gluey areas are 86, 88, and 90.

When wrap 84 is worn, area 86 will match and stick to the back part of an area 92 after the upper part of the wrap has been wrapped around the lower abdomen. Area 88 will match and stick to an area 94 after the lower right part of the wrap has been wrapped around the right upper thigh. Area 90 will match and stick to an area 96 after the lower right part of the wrap has been wrapped around the left upper thigh.

Wrap 84 has a rectangular area 98 to register with part 26 of main wrap 20. Area 98 can be cut open and folded to the upper and lower sides (or torn) to make a window through which part 54 can touch part 26 of wrap 20 to hold balloon 36 in place. If wrap 84 is used to cover the area under the balloon, then there will be no need to have this window opened.

Wrap 84 may consist of a sheet of plastic to prevent oozing of the blood or liquids outside of the wrap. It may be designed to attach inside of the outside wrap by way of snaps, gluey surfaces, or clips, etc., before its use. The sizes, relative shapes, color, and materials of wrap 20 may vary to match different people's size and body structure as well as the amount of the pressure needed for the job to be done. The shape of the balloon and its cover may be modified to fit the anatomy of the groin area in different people with different groin anatomy, and it could be wider or have a longer diagonal along the femoral artery to cover the lower part of the abdomen for the patients whose perforation of vessels is done over and above the groin areas.

Some parts of this wrap such as the cover for the left groin and the left thigh may be eliminated when the wrap is made to be used for right groin procedures, and vice versa. Further support can be achieved for higher pressure by adding hard plastic or metal sheets to the wall of the area over the groin to enable it to stand higher pressure. The shape of these sheets may be oval or quadrilateral with mild curvature in center to match the shape of the balloon. These hard sheets may be permanent parts of the structure of the wrap or inserted inside a pocket over the groin area in the wall of the wrap when needed.

In some models, the area over the wounded vessel can be made from transparent plastics to give the chance of watching for bleeding. In such cases, the Velcro TM part 54 will be removed from the area.

FIGS. 11 and 12 show a clear transparent plastic tube 100 with 5 by 10 mm outside size and about 2 by 5 mm inside opening and 25 to 30 cm length, designed to resist pressure and to hold a hydrophilic cotton yarn or mesh 102 inside. One end of this mesh will be positioned directly over the wound area, and the tube will extend to other end to be exposed for observation outside of the wrap. This mesh is to absorb the blood if it oozed and carry along inside the tube to allow the blood to be noted and bleeding to be observed.

When properly placed in the area after a procedure, i.e., cardiac catheterization, the balloon will be over the artery which was intervened and then, after inflation, it will put the appropriate pressure desired in the area to prevent oozing of the blood. The pressure is easily controlled and it can be checked by a gauge. A mesh inside a plastic cover to be located under the balloon may help to notice bleeding, with absorption of the blood by the mesh and discoloration of its white color when contaminated with blood.

Further support when needed can be provided with the use of a hard piece of plastic or metal located over the balloon and inside a pocket in the wrap, or in the space between the wrap and the balloon.

The balloon 36 inside cover 40 may be enough to work in some cases alone without an outer wrap 20. A soft disposable cover may be made to cover this piece in order to prevent contamination.

In summary then, the disclosed balloon 36 and its cover 40 may be said to comprise a face 56 that confronts the person's groin line and portions of the person's abdomen and thigh on either side of the groin line. The vertex 58 fits into the groin, dividing this face 56 into an abdomen-confronting portion and a thigh-confronting portion. The balloon and cover have a length extending between tubes 50 and 52, a thickness that extends in the direction of pressure application to the underlying wound, and a width that is transverse to both the length and thickness.

Figure 13:
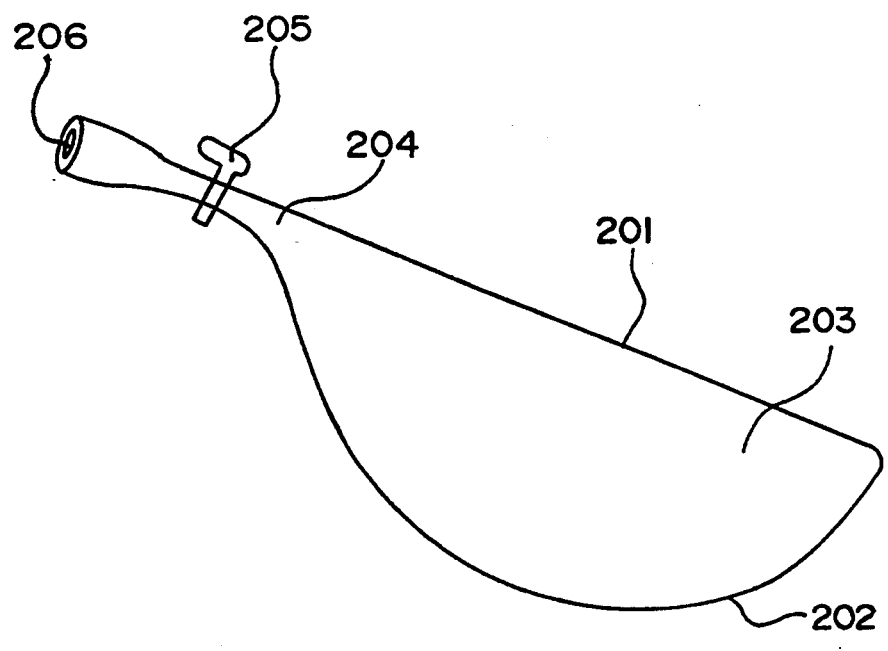
FIG. 13 is a top plan view of another balloon.

FIG. 13 shows a balloon having a straight upper rim 201 and a curved lower rim 202. The front surface is 203, and the inflation port 206 is shown with a short inflation tube 204. A three way stopcock 205 is also shown.

Figure 14:
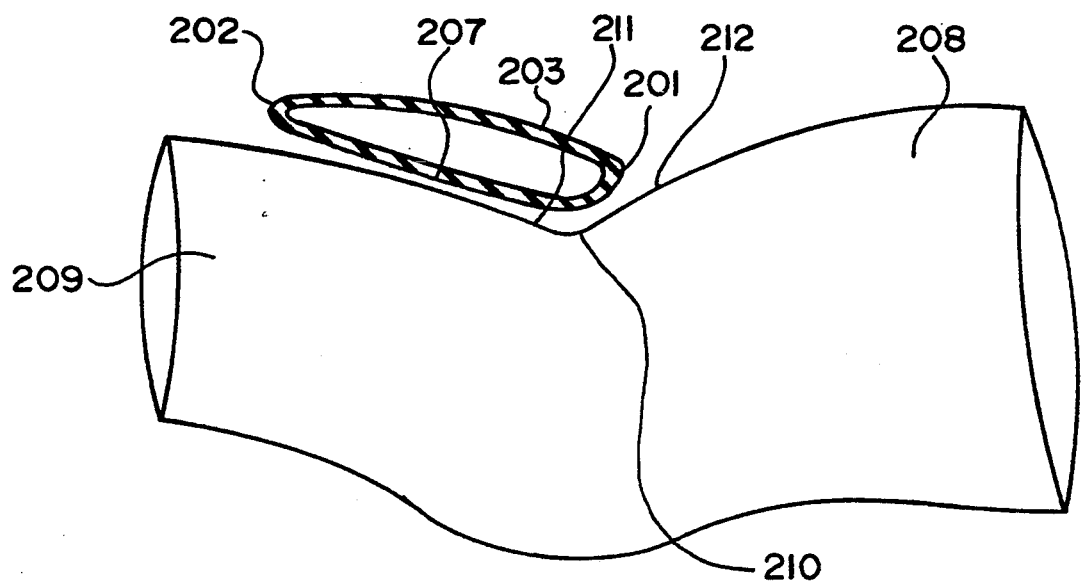
FIG. 14 is a side elevation of the balloon of FIG. 13 showing use.

FIG. 14 shows the balloon of FIG. 13 when it is placed at the site of a procedure. Here the trunk is shown by 208, the right thigh by 209, the groin line by 210, the surface of the lower abdomen near the groin line by 212, and the surface of the upper thigh near the groin line by 211. The lower surface of the balloon is shown by 207. This figure shows the general position of the balloon compared to the groin area.

Figure 15:
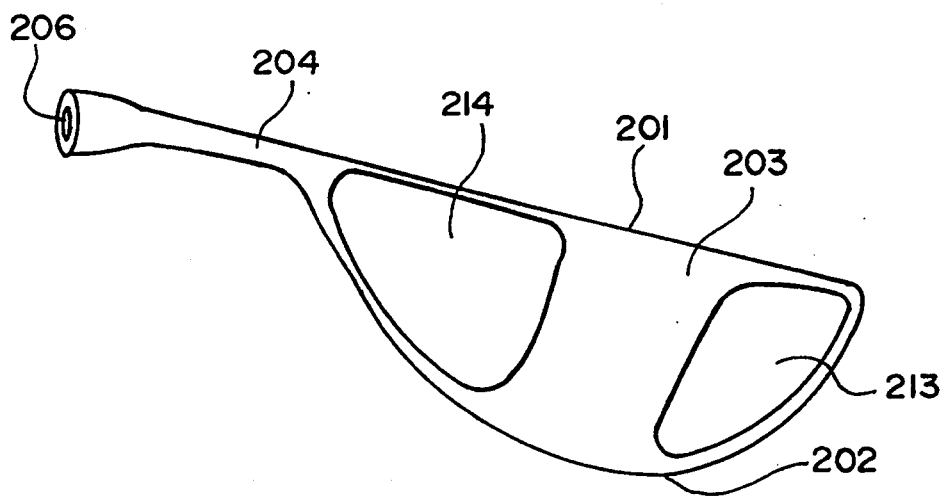
FIG. 15 shows a modification to FIG. 13.
Figure 16:
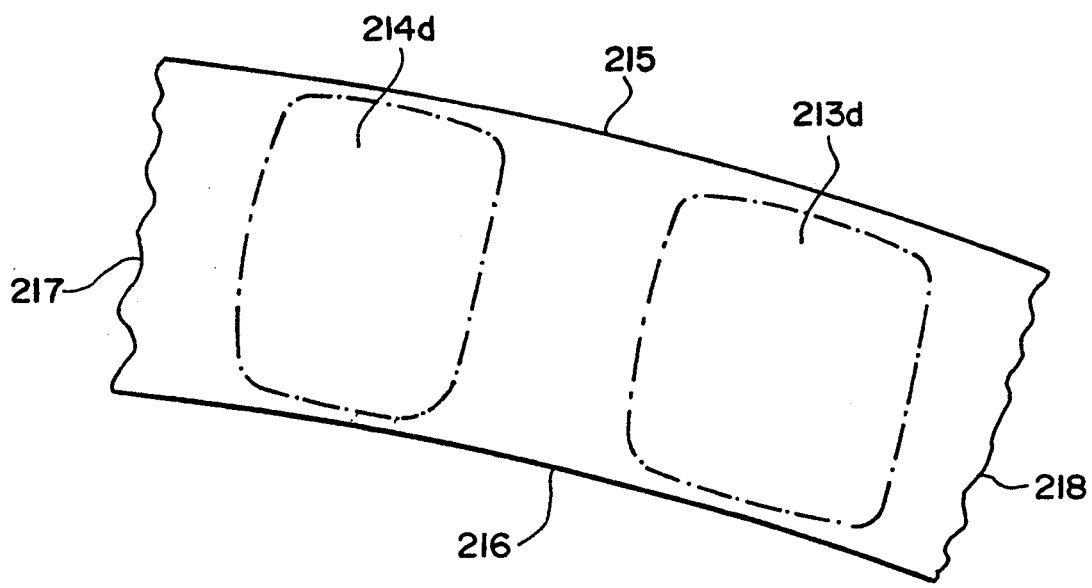
FIG. 16 shows a plan view of a portion of a support system for the balloon.

FIG. 15 shows a balloon similar to the one shown in FIG. 13, except this balloon has two patches of Velcro TM on its top surface, here shown by 213 and 214. These are to match and be stuck to matching Velcro TM patches of a support cover shown in FIG. 16 that stands on top of the balloon. The upper rim of this support wrap is shown by 215, its lower rim by 216, the cut of its right edge by 217, and the cut of its left edge by 218. The matching patch for patch 214 is 214a, and the matching patch for patch 213 is 213a.

Figure 17:
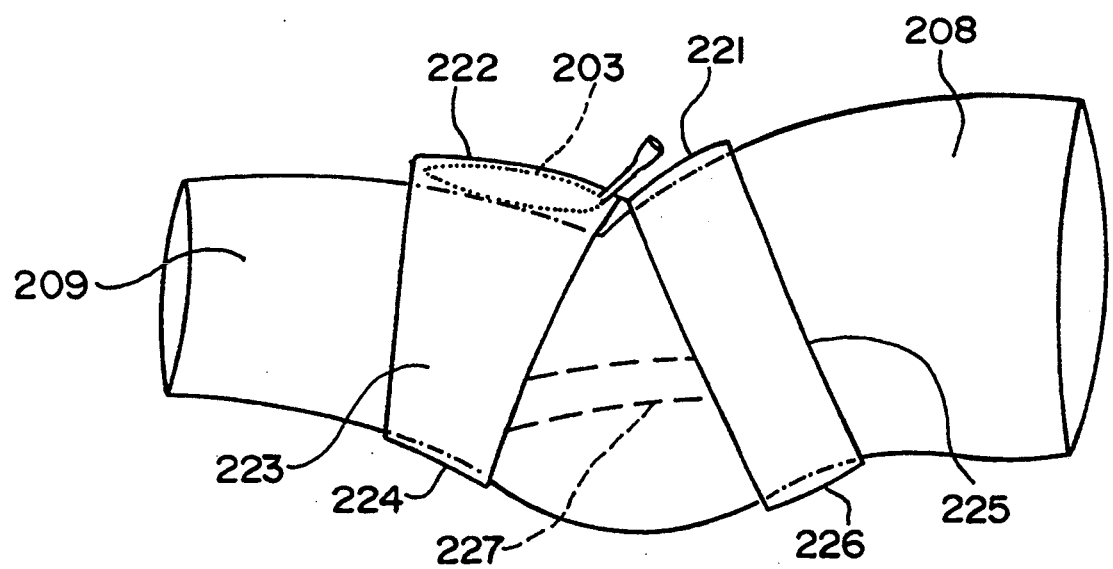
FIG. 17 is a side elevation showing use of the support system.
Figure 18:
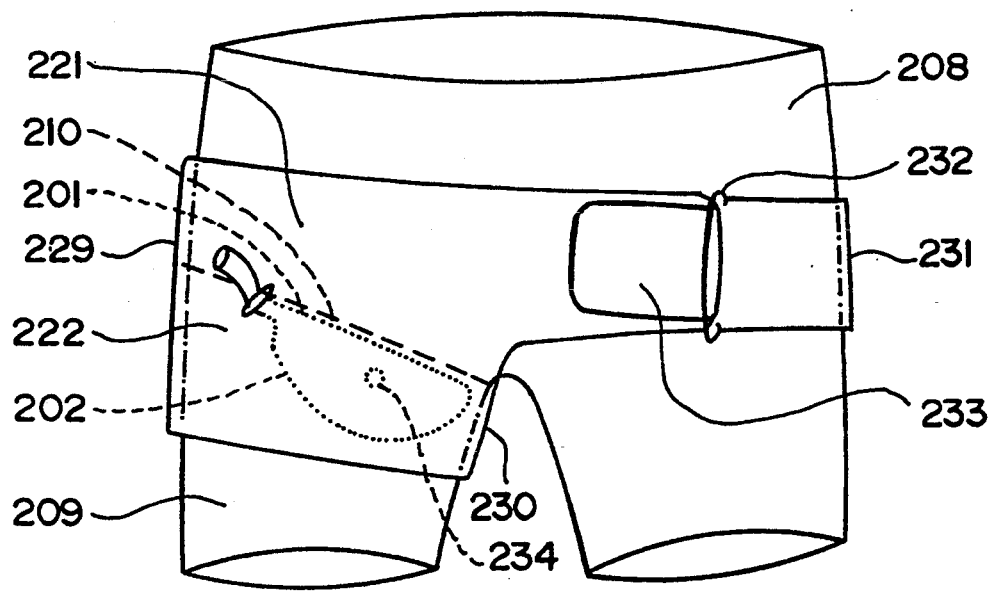
FIG. 18 is a top plan view of FIG. 17.

FIGS. 17 and 18 are to help the reviewer notice the placement of the balloon and the wraps holding it on the body. The balloon is placed on the upper surface of the right thigh, and it is held in place by a wrap that goes around the thigh as well as the waist area. The upper surface of the wrap over the balloon is shown by 222. The inner side of the wrap which is around the right thigh is 223; the part under the right thigh is 224; the part on the lower abdomen is 221; the part that is in the side of the waist is 225; and the lower part of the wrap under the waist is 226. Please notice that in this view for the purpose of presentation, the left thigh is not shown at all.

FIG. 18 shows the front view of the balloon and the wrap in place on the body. The balloon is placed on the upper surface of the right thigh, immediately under the groin line 210. The hole in the skin is shown by 234. The upper wrap goes around the waist, and 231 shows the left side of the wrap. 232 shows the snap that the end 233 of the upper wrap goes through to make a U turn and come and stick to a matching Velcro TM patch on its own rear surface. The front part of this wrap continues in the right groin area to cover the surface of the balloon and then to wrap around the upper thigh at 222, the right side of this part being shown by 229 and the inner part by 230.

Figure 19:
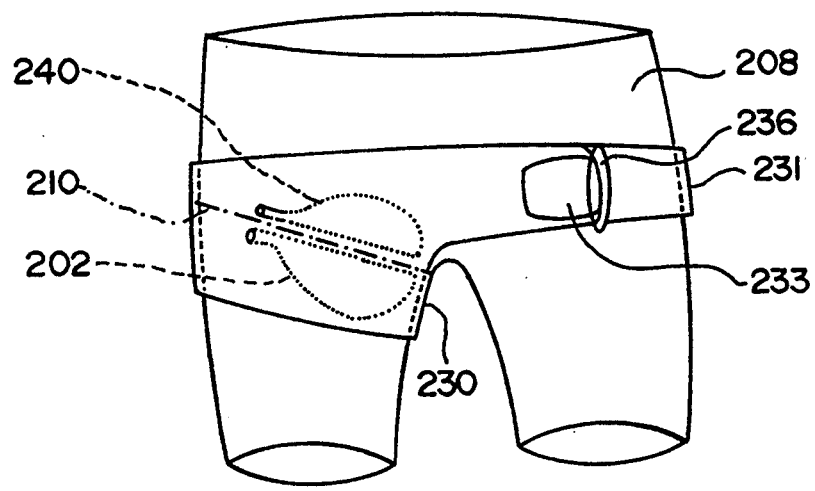
FIG. 19 is a top plan view, similar to FIG. 18, but showing a further balloon.

FIG. 19 is very similar to FIG. 18 except here the balloon is a double balloon, one shown by 240 standing on the lower abdomen, and the other being the balloon of FIG. 13 standing on the upper part of the groin. The upper wrap goes around the waist, with 231 showing the left side of the wrap. 236 shows the snap that the end 233 of the upper wrap goes through to make a U turn and come and stick to a matching Velcro TM patch on its own rear surface. The front part of this wrap continues in the right groin area to cover the surface of the balloon and the inner part of this wrap is shown by 230.

Figure 20:
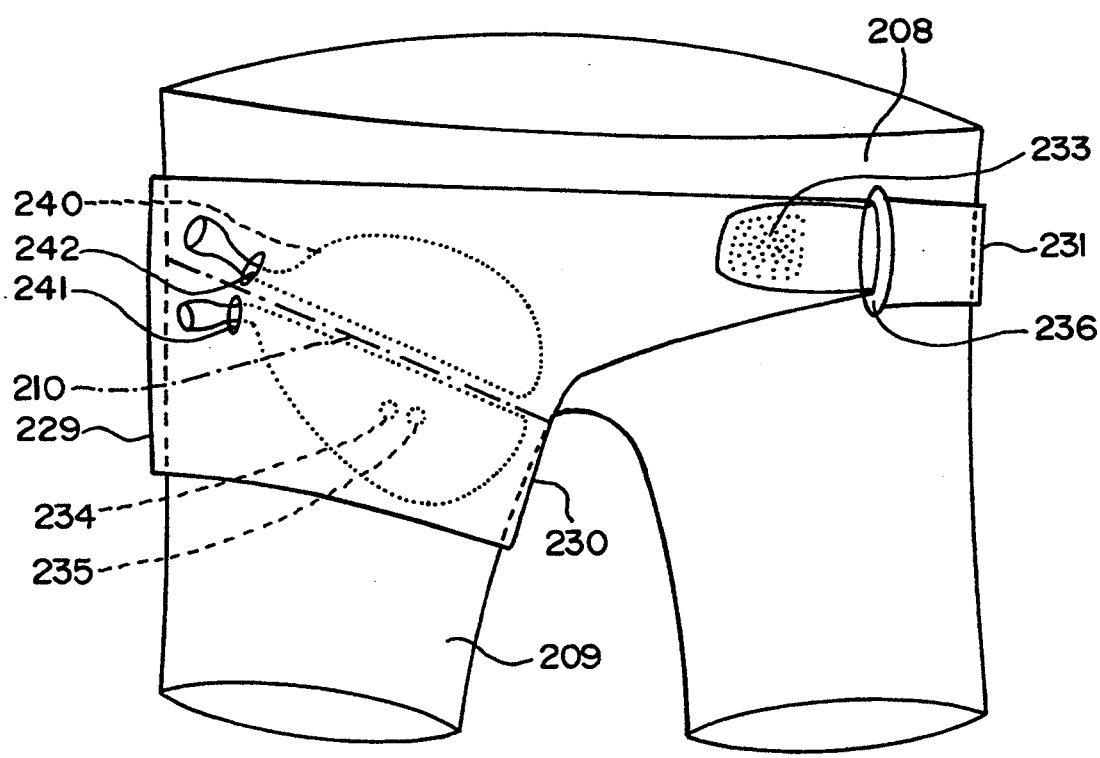
FIG. 20 is an enlargement of FIG. 19 to show more detail.

FIG. 20 is larger to show more details. The lower balloon is standing on the upper part of the groin over two holes in the skin shown by 234 and 235. The outer side of the wrap that covers the lower balloon 229, and the inner part of this wrap is shown by 230. The inflation ports of the upper and lower balloons have gone through the holes 242 and 241 respectively to come out of the wrap. These holes 242,241 are in the wrap.

Figure 21:
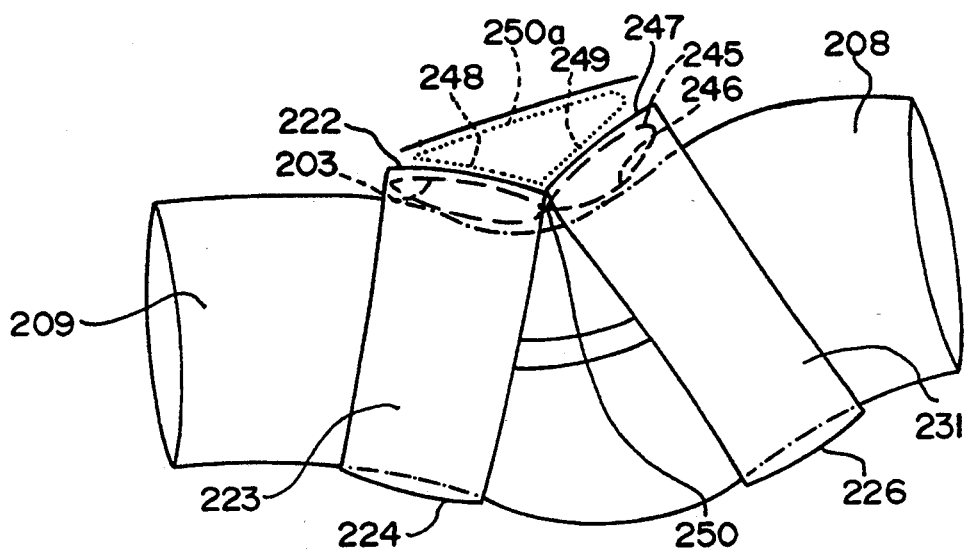
FIG. 21 is a side elevation of usage like FIGS. 19 and 20, but showing a still further balloon.

FIG. 21 shows the lower balloon connected to the upper balloon by a connection piece 250. The upper balloon is placed on the lower abdomen immediately above the lower balloon. The upper surface of this upper balloon is shown by 245 and the lower surface of it by 246. The lower balloon is held in place by the lower part of the wrap. This wrap goes around the thigh as well as the waist area. The piece of the wrap over the upper balloon is shown by 247, corresponding to 221 in FIG. 18. Left thigh is not shown.

Figure 22:
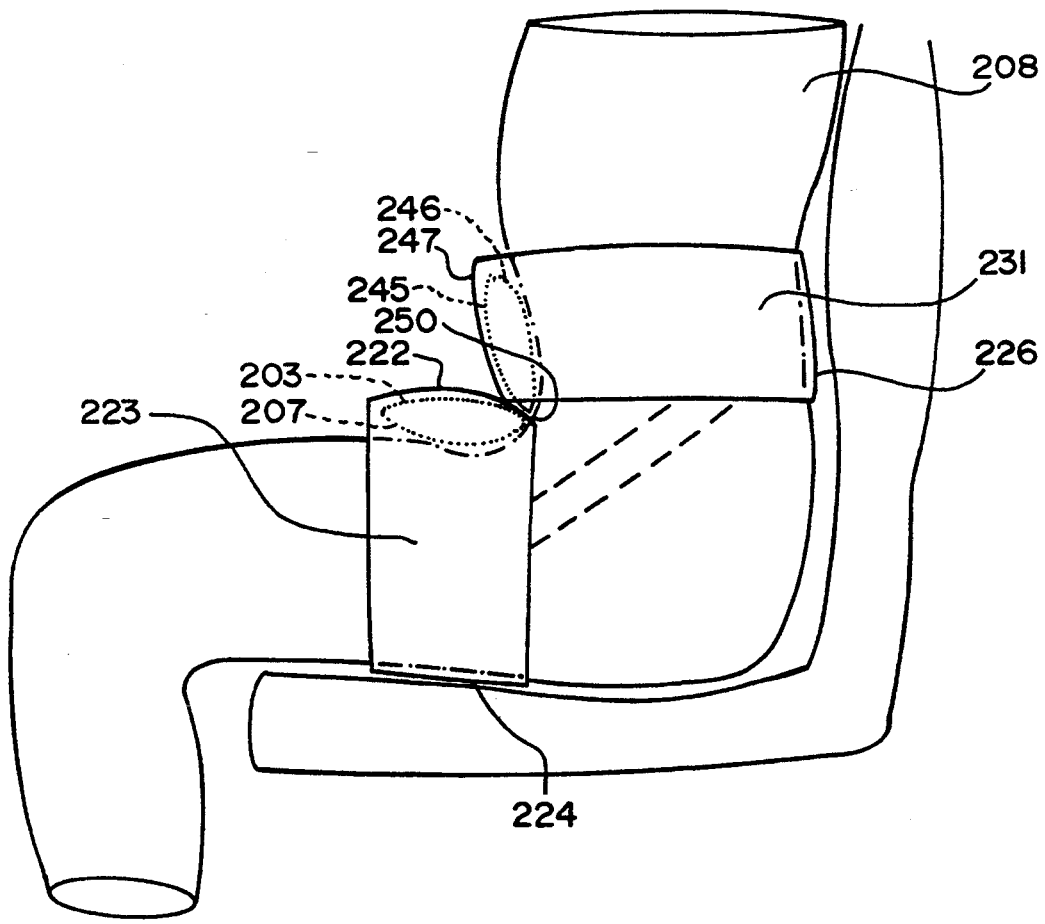
FIG. 22 is a side view showing how a patient can sit up with my invention.

For the purpose of FIG. 22, the left thigh is also not shown. FIG. 22 is to illustrate the benefit of this unit when the person is using it. Here the patient is sitting on a chair. The thigh has a 90 degree angle with the trunk. Here again double balloons are in place, held by a wrap that is not continuous and connected in the back to allow the person to sit comfortably. In this view the lower balloon is on the upper surface of the thigh; the upper balloon is on the lower surface of the abdomen; and both of them are held in place by the wrap.

Figure 23:
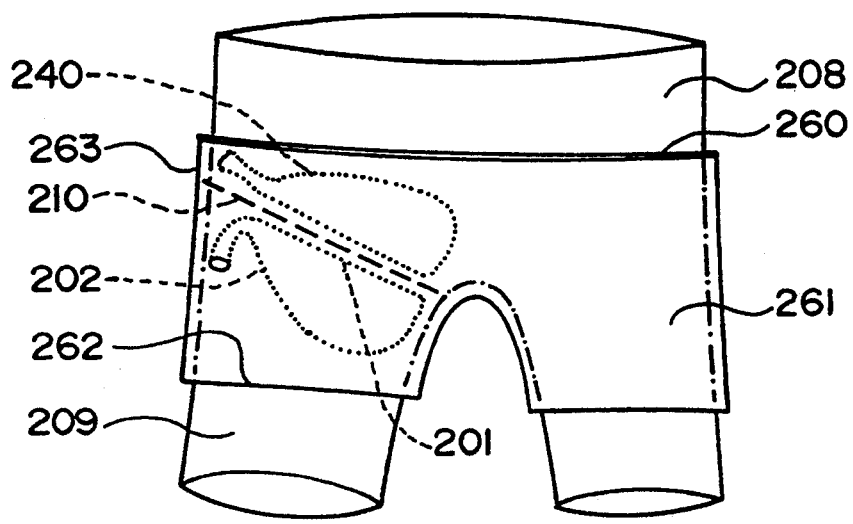
FIG. 23 is a plan view showing usage of balloons with shorts.

FIG. 23 is very similar to FIG. 19 except FIG. 23 is to give an idea about the shape and construction of shorts used to hold the balloons in groin and lower abdomen area. Here the balloons are like those of FIGS. 19-22. The upper part of the shorts is 260; the right side is 263; the right leg of the shorts is 262; and the left leg of the shorts is 261.

Figure 24:
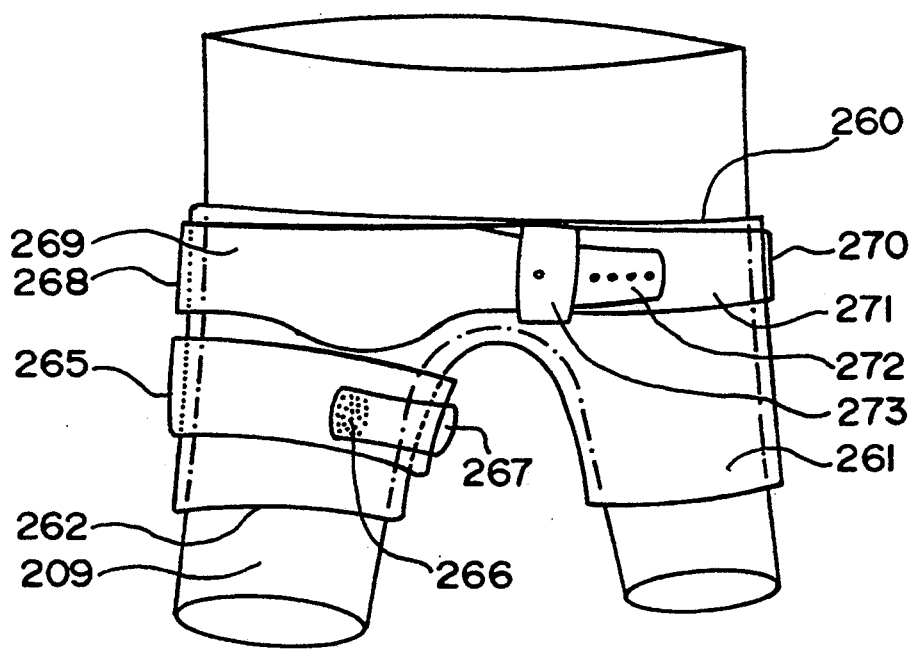
FIG. 24 is a view similar to FIG. 23 showing the addition of wraps.

FIG. 24 shows the outlook of the shorts shown in FIG. 23. In this view the patient is wearing the shorts. Here an upper strap is shown by 269; the right side of the strap by 268; the left side of the strap by 270; and the end 272 of the right side of the strap comes and goes through a snap 273 at the end of the left end 271. A lower strap 265 has an end 266 that makes a U turn on a snap 267 and comes and sticks to its own back.

Figure 25:
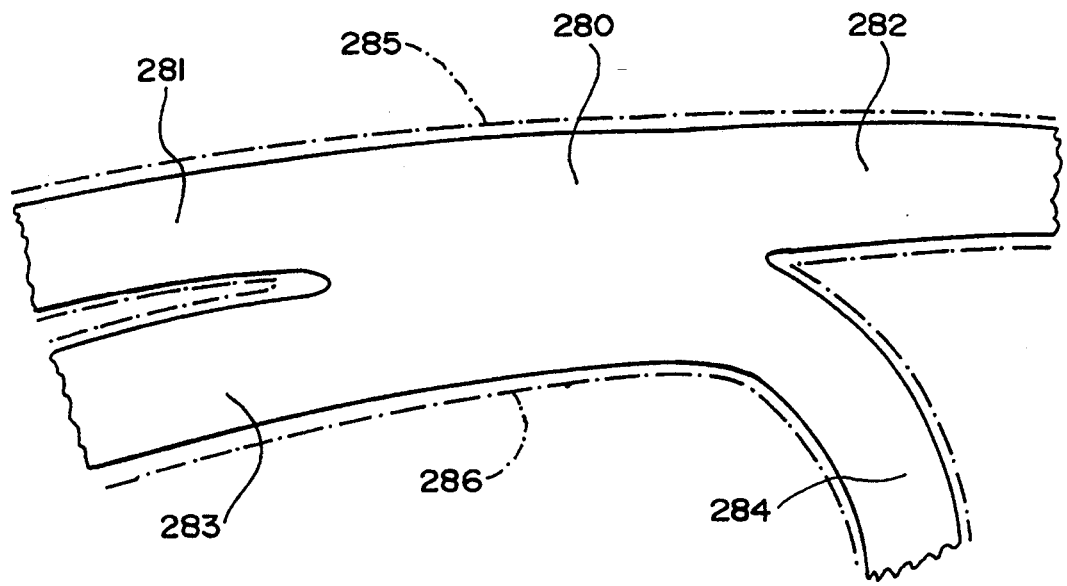
FIG. 25 is a plan view of a portion of an inner cover.

FIG. 25 shows the front outlook of an inner cover, as laid on a table. 280 shows its body which will stay on the front of the patient over the upper groin and lower abdomen. 281 and 282 are pieces that will stay under the upper wrap or strap (the total length is not shown), and 283 and 284 will stand under the lower wrap or strap. This figure shows a rim 285 as well as a rim 86; their border is shown by a dot and dash line. This rim is to overlap the edge of the support cover and is to be turned to stick to the back of the rim of the support system to prevent the edge of the support system from irritating the skin of the patient. The surface of this unit may have bands or patches of adhesive or Velcro TM.

Figure 26:
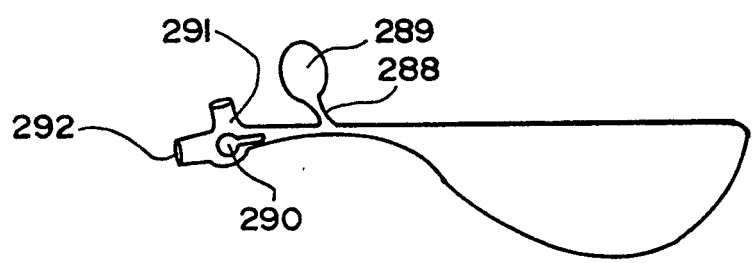
FIG. 26 is a plan view of a balloon with a pressure indicator.

FIG. 26 shows the general look of a balloon similar to the one shown in FIG. 13. FIG. 26 is primarily to show a small balloon 289 that is connected to the inflation tube for the purpose of showing the pressure inside the larger balloon. Balloon 289 has a connecting tube 288 as shown. The main balloon ends with a three way stopcock having an end 292, a side opening 291, and a control arm 290.

Figure 27:
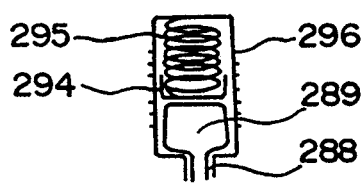
FIG. 27 is a cross sectional view through the pressure indicator on a larger scale.

FIG. 27 shows a unit which provides some measurement of the pressure inside the balloon. This unit is made from a clear plastic cylinder 296 that has the small balloon 289 inside. This balloon 289 is standing against the flat cover 294 of a spring 295 so that when the pressure of the air inside the balloon 289 is increased the flat cover of the spring moves and squeezes the spring. Its movement can be seen through the clear plastic wall of the cylinder to give an approximate idea about the inside pressure. The side of the clear plastic will be marked and standardization may be made against a mercury sphygmometer, which will give a rough idea.

Figure 28:
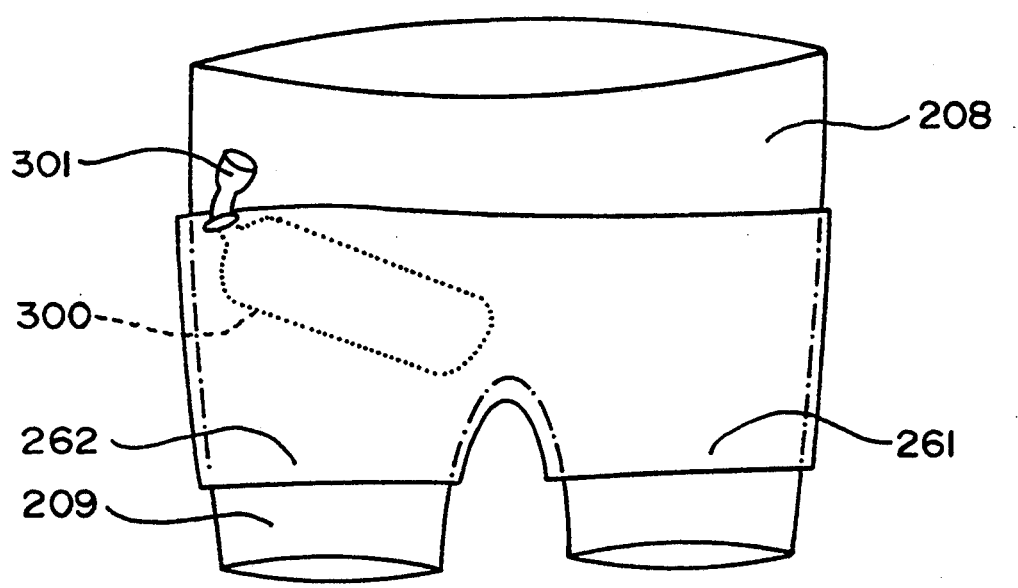
FIG. 28 is a plan view of an embodiment for treatment of hernia.

FIG. 28 is very similar to FIG. 23 except this view is to give an idea about the shape and construction of a shorts that is to be used on patients with inguinal hernia. Here the balloon has a shape more like a rectangle, and it also has the curve to match the area (not shown here) and is to stand on the hernia area. The balloon 300 is shown with dotted line, and its inflation port by 301.

Figure 29:
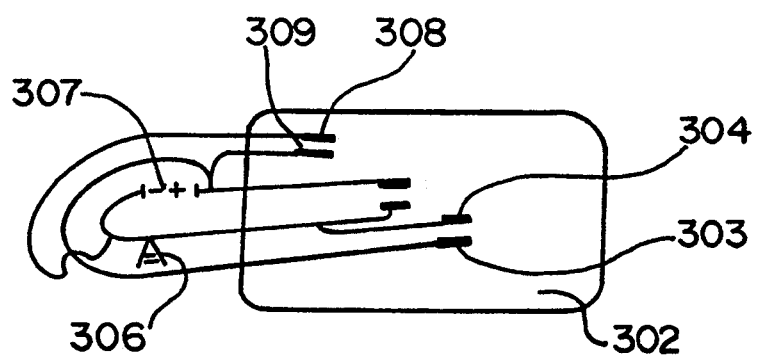
FIG. 29 is a schematic diagram of an electric system and alarm for detecting wound bleeding.

FIG. 29 illustrates the unit which is for sensing contamination by blood. In this view the body of a cover is shown by 302. Electrodes 303 and 304 are connected to a battery 307 and an alarm 306. Here three pairs of electrodes are shown, one in the middle which is not marked, and another pair 308, 309 which is standing further than the other ones. The idea is to have different levels of these sensor leads that one of them may be activated to indicate bleeding. The switch for turning them off is not shown here.

Figure 30:
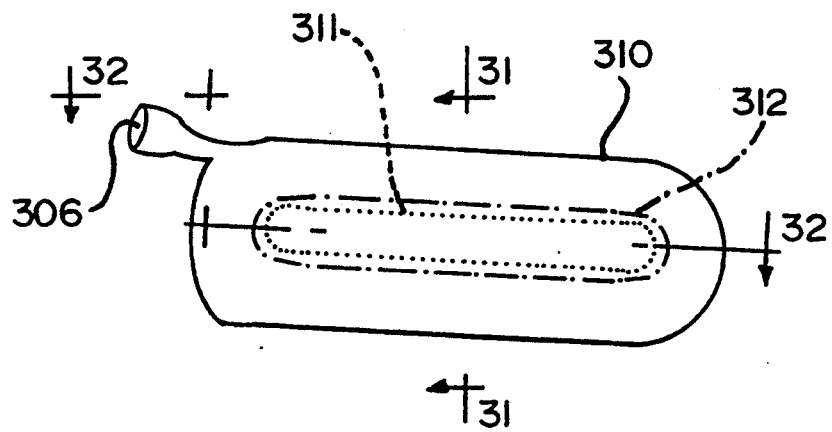
FIG. 30 is a plan view of another form of balloon.

FIG. 30 is a balloon that is to be used after hernia surgery (it can also be used in other surgeries) and during the period that the site of incision is still sensitive. This is a unit that has a shape to match the area of the hernia. The dotted line in the center 311 is to show the area to be protected from the pressure of the balloon by a rigid or semi-rigid plastic shown by 312. Here the inflation port 306 is shown, as well as the border of the balloon by 310. This figure gives a general idea about the shape of the balloon although it may have different shapes and sizes.

Figure 31:
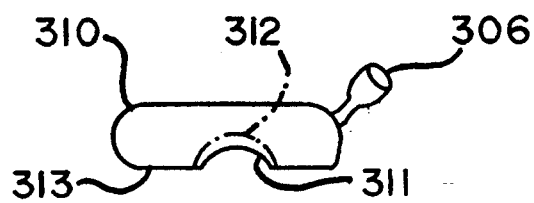
FIG. 31 is a transverse cross section through the balloon of FIG. 30 along line 31—31 in FIG. 30.
Figure 32:
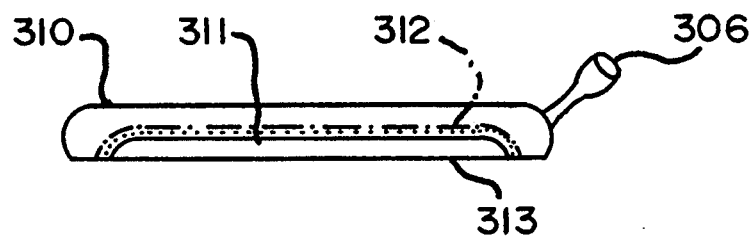
FIG. 32 is a longitudinal cross section through the balloon of FIG. 30 along line 32—32 in FIG. 30.

FIGS. 31 and 32 show the lower surface 313 of the balloon, the curved protective area 311, the outer surface of the rigid or semi-rigid protective plastic piece 312, and the border 310.

Detailed Explanation of FIGS. 13-32

Reference is made to my pending applications Ser. No. 07/800,085, and Ser. No. 07/967,379, especially FIGS. 22, 23, 4, 25, 26, 15, and 16, and pages 33-34 about units for herniorrhaphy and pages 37-38 under the title, "Use of this unit after Coronary Angioplasty" in the latter As mentioned earlier, both physicians and patients are deeply concerned about complications at the site of intervention in the groin after cardiac catheterization and related procedures such as angioplasty. I believe the need for protection and peace of mind is real. This concern is such that usually there are some statistics about the complications of cardiac catheterization in each cardiac center, and the lower it is, the better is sounds for the institution. But to the best of my knowledge there is no unit available for protection of the groin that a patient can take home, except my own previous invention under the above patent applications, which is now being modified and improved in this application.

Basically FIGS. 13-32 is a unit that, like my previous inventions, uses a specially shaped pressurized balloon to prevent bleeding in the groin area after cardiac catheterization and related interventions. This pressurized balloon is designed to be held in place by use of special straps, wraps, or shorts. However I have reached to conclusion that in some cases, use of the previously mentioned single balloon would not be as effective. During transportation and times that a patient has to sit on a chair, a single balloon going from lower abdomen to upper groin may cause problems such as disfiguration and possible dislocation of the balloon and wrap and potential malfunction. This is due to the fact that the pressurized balloon may not bend easily in the groin area when it is held in place by a wrap. Again this may cause dislocation of the balloon which may cause the balloon to be less effective and not to serve the important intended purpose. So in my mind this cannot be used in patients who are going to sit on a chair during and after discharge. Therefore in order to provide a patient with a functional unit that can be used outside of the hospital or clinic, an improved version of my previous model is presented here. This modification and improvement contemplates the use of one, two or more balloons with special shapes that allow the patient to assume sitting position without much discomfort. The modification also applies to the support system as well that will have a shape that allows patients to sit without much disfiguration and lack of function of the unit.

Also during many years of my practice I have noticed the great concern of patients with hernias about their problem and their worries about whether their hernia may enlarge, deteriorate, etc., with different motion. I have noticed that this concern and anxiety are real, and there is a big difference in mentality of different people, and their situations. The surgery for hernia, although very useful and beneficial, and most of the time simple, cannot be done all the time since the timing for all patients may not be feasible due to concerns such as acute major sickness like heart attacks, terminal cancer, or severe lung disease, etc. These may not allow a patient to have surgery as a person may wish, and so a temporary alternative will be very useful many times. Also after some surgery when the constructed tissues are still weak, use of support can be very useful and beneficial. For these reasons I believe with minor modification of this unit a unit can be made to support the area of the hernia in many cases.

For this purpose a unit can be made with a longer balloon (300, FIG. 28) to be held over the inguinal hernia area and operated site by a support system after the surgery. In such cases the pressurized balloon is held by a wrap to prevent the hernia from bulging and the site of operation to be pressured by the intra-abdominal pressure.

As I have specified in my previous application, (pressure bandages and dressings), the center of this balloon may be made to have a free space along the line of incision shown by dotted line 311 to prevent pressure to the incision site when it is tender and sore. This area can be protected by a piece of rigid or semi-rigid plastic shown by dot and dash line of 312. The fact that the balloon itself, its location, and the pressure inside the balloon can be changed easily gives freedom and many choices for this unit. This can be very helpful in different circumstances when there is a need for support and pressure changes. For example, we can imagine the case of a patient with hernia who develops a case of severe cough due to bronchitis, as many people do. During the episodes of severe cough, there is a greater need for support than in a relaxed normal condition. Or if a person with hernia is to move heavy objects manually, that will automatically increase the pressure inside the abdomen. Again, the need for support increases and therefore my invention turns out to be very useful by giving adjustability and options. This technique with minor alternations may be also used and be beneficial in the other cases of abdominal hernias for physical and psychological support.

Special shorts can also be made to have a pocket to hold the balloon and to be kept tight by one or two straps. That will allow the patients to use them easily and practically whenever they wish and not to worry about their hernia popping such as in some of my patients. I believe that use of this unit will bring significant peace of mind to these patients as well as providing significant (although temporary) protection.

The Balloons and their Shape

This unit is made from one (FIGS. 13 and 14) or two balloons (FIGS. 19-22), each having a shape similar, but not identical to, a half moon. The balloons or their cover may be connected to each other by a band or fabric along their straight line edge. They may also be used as two separate and independent balloons. In some cases use of one lower balloon may be sufficient (FIGS. 13 and 14), that in that case, the balloon has a line 201 that matches the direction and shape of the groin line 210 and is held close to it. The exact placement of this balloon will be related to the case and the judgment of the physician. This balloon has a lower rim or edge 302 that is somewhat similar to the curve of edge of the half moon, although the inner half side of this balloon is wider with more surface than the outer side. This is to cover the length of the vessels under this area. From the other side, the thickness of the balloon close to the groin line (close to 210 in FIG. 14) will be much thicker to fill the deeper space which exists in the groin line area. This shape by itself is important and I believe gives a great advantage to this balloon to function much effectively. The upper balloon (240, FIG. 19) is very similar to the mirror image of the lower balloon. With some differences that can be noted in FIGS. 19 and 20, the lower balloon is placed on the area where the intervention has taken place and needs to be pressed. The upper balloon is placed on the lower abdomen over the main vessels going to the thigh area. These balloons will have an inflation port that will allow the air to be inflated, and one rubber hose (not shown in figures) may also be connected to the balloon to allow connection to a pressure monitor of one kind or another to allow monitoring the pressure. Importantly in some cases, fluids such as iced water may also be injected, or pumped, into these balloons. In such cases the second balloon will let the air to be taken away. For this case, the balloon will be made from appropriate material to tolerate the cold temperature for such use. Some air may still be left inside the balloon for application of pressure. The use of iced or cold water is to help to prevent more oozing of the blood in some cases. A person may wish to use warm water later. A three way stopcock or a valve (205, FIG. 13 and 290, FIG. 26) are used to prevent air or fluid leakage. The three way stopcock may be connected to the very tip of the inflation port to allow the control. A one way valve (not shown in picture) may be used instead in the tip of the inflation port of the unit so that it will allow injection or suction of air or fluid into the system to occur but not to allow the air to move in and out after the inflation syringe or balloon is disconnected.

These balloons may have a patch of Velcro TM or adhesive film on some part of their surface to allow the balloon to be stuck to the matching pieces of Velcro TM from the support system so that the position of the balloon can be adjusted relative to a patient and the support system, considering the anatomy of the area as well as the site of intervention, etc. This design will be helpful since there is significant variability between the size of the people and shape of their groin area due to height, weight, truncal obesity, etc. For this reason there will be different sizes and shapes of these balloons to allow one particular one to be chosen for a given patient.

When two units are used, one balloon will stay in the upper part of the groin and the other one in the lower part of the abdomen. The inside of these balloons may be connected to each other so that they could be inflated by one inflation port or most commonly they will have two different openings for inflation so that different pressure build up can occur in their cavities. The balloons may be connected to each other along their straight edges by way of straps or bands or continuation of their surface material. Alternatively a piece of wide adhesive tape can be used to tape these two balloons to each other, after their position is chosen. In the cases where the balloons are connected (FIG. 21 and 22), the connection line 250 will be thin to allow the bending to occur along that line when patient assumes a sitting position.

The use of two balloons will allow the patient to bend his or her leg while sitting in the chair, and the space between the balloons lets such function to occur while the pressure is still being applied to the areas under the balloons on upper and lower sides of the groin line. Sitting position will be assumed most of the time during transportation by wheelchair, car, etc., and this is the time that this unit shows its significant advantage over my previous invention. Also in order to apply enough pressure when patient is in supine position a third balloon 248, 249, 250a, FIG. 21, may be used that will go over those two balloons like a wedge and stay in the area between them so that the balloon can expand and fill the space and gap between the upper and lower balloons to deliver extra pressure needed for better function when patient is in supine position. This will be an optional use.

The Choice of Balloons

The fact that this application mentions three balloons will bring the question of when these are needed to be used and if they are the same. For this reason I explain the following:

1. The single balloon is to be used when the patient had simple cardiac catheterization and the area looks very much clean without much hematoma or complication.

2. Double balloons are recommended when there has been significant work done in groin with possible hematoma and extravasation of the blood during cardiac catheterization. This unit is recommended in all cases of transcutaneous angioplasty in which the size of the sheaths are larger and the intervention is usually much more intensive.

3. The third balloon is to be used when a patient is in supine position and when extra pressure seems to be necessary.

The Support System

In order to hold these balloons in place and to apply pressure, different techniques are chosen as follows:

A. Use of Straps: The balloon may be made with a cover that has a tight non-stretchable cover in its rear side (that is to stay away from patient). This is to allow the application of pressure in the area. A softer more stretchable cover in the front (that is to stand against the wound area and this construction will allow the transmission of the pressure to the wound area). The outer cover of the balloon also has an extension like a flap that is to stand on the lower surface of the abdomen and to be held in that area securely and tight by connection or the overlap of a strap or wrap that goes around the waist. The side ends of the balloon cover are connected to a pair of straps that go around the groin to be held tightly in place. The straps are connected to each other by snap or Velcro TM patches. These straps are soft and non-stretchable, similar to the material used in cars' seat belts. These straps will hold the balloons in place securely and comfortably.

B. Use of Wraps: The balloon may be kept in place with use of wraps (FIGS. 17-20) that go over the balloon/s and to give the chance of building pressure against it. This wrap will go around the groin (229, 230, FIG. 18) and the waist (221, 225, 226, FIG. 17) and (221, 231, FIG. 18) to be held in place tight. Their ends to come together to be held in place by snaps or Velcro TM patches (232,233, FIG. 18). Here again in order to have the unit study as well as comfortable and ideally functional the wrap has a shape that is connected in front, but separate in the back (FIGS. 17-22) so that very importantly the waist part is allowed to separate from the groin part when patient is sitting on the chair. The upper part of the wrap (247, 231, 226, FIGS. 21, 22) goes on the waist area and the lower part (222,223,224, FIGS. 21, 22) go as around the upper part of the groin to hold the unit in place securely and comfortably.

C. Use of Special Shorts: A special shorts (FIGS. 23, 24) may also be made to hold the balloon in place and be supported by straps. This will be very practical and easy to use in some patients. This shorts will be made from cotton or similar material used in making regular shorts, except it will be slightly tighter and have a pocket in the right or left groin area (wherever the procedure is done, most commonly the right side) where the balloon is supposed to stand. This pocket has a size and shape to accept and hold the balloon inside it. This pocket (not shown) has a means for holding the balloon inside itself securely by way of a zipper or a flap with buttons, etc. There can be means for adjusting the size of the pocket by way of having different buttons or holes in the flap and side, or similar way, or use of Velcro TM patches, so that to some degree the position of the balloon could be changed. A strap (268-271, FIG. 24) is connected to the outside of the shorts to allow it to go around the waist like a belt and to be tightened in place by a belt-like system (272, 273, FIG. 24) that looks like a belt. Also another nicely made strap goes around the thigh area (265, FIG. 24) over the shorts and balloon and is tightened by Velcro TM patches (266, 267, FIG. 24). A fake strap may also be made in the left side to make a design so that people will not look at it as a therapeutic device and so that patient may walk with it in warm weather. This combination may not only be easy to use, but easy to accept and tolerated by some patients. The balloon may be incorporated in the wall of the shorts in the factory before delivery to the hospital. The shorts may also have a design for use with two balloons (FIG. 23) which would need the incorporation of pockets for two balloons: one higher pocket in the lower abdomen area; one lower in the upper groin area; and both of them to be supported by straps as mentioned. In order to control the position of the balloon relative to the straps and wound in models where the balloon is tightly placed inside the pocket of the shorts, the outside of the pocket has a patch of Velcro TM. The inner surface of the straps has the matching piece of Velcro TM so that the attachment of the strap on the pocket when the balloon is appropriately placed holds the balloon securely in place as desired.

These shorts may also have a layer of thin plastic inside to prevent leakage of blood or fluids in and out of the wound place. These shorts will be made in different sizes, shapes, and colors to allow selection and matching of the best one for a given patient. These shorts may have an opening in the front to allow urination without removal, and they may also have a flap in the back that can be opened to allow defecation to happen in certain circumstances where patient is not able or should not take the unit off and put it back easily. In such cases after the patient had a bowel movement, a small pad is placed on the anal area to prevent contamination of the shorts until more appropriate cleaning will be available for the patient. Obviously, this is for unusual circumstances that may occur for a certain patient, but it can be very useful in that circumstance.

FIGS. 26 and 27 will give an idea to the patient to watch for pressure loss. This can also be done by a plastic balloon having a mixture of air and water inside instead of the spring so that with pressure the air is compressed to allow the movement of the flat surface to occur and the measurement to be made.

Alternatively the unit can be connected to a presently available sphygmometers to have the pressure of the balloon to be measured, or a presently available device may be used for such purpose.

The Inner Wraps

This is a wrap (FIG. 26) made from a soft, comfortable, absorbent material, such as clean and sterile cotton, that matches and fits the size and shape of the support unit and is slightly larger (due to the rims 285 and 286) to prevent the support unit from touching the bare skin. This inner cover is to give good feeling to the patient as well as providing sterility and cleanness to the area and the system. This unit will wrap around the patient and may have bands of adhesive film on it, in its rim, and different parts of the cover as desired. This film of adhesive is covered by a thin plastic layer that is removably stuck to it and will be removed at the time of use to allow the inner cover to be placed over the skin under the wrap. The rims of this cover can be turned outside to go over the edge of the support system to prevent it from hurting the skin of the patient. This inner cover may also have a thin plastic layer on its outside to prevent from leakage of blood to the pants and shirt, etc.

The Directions and General Informations About the Way this Unit Should Be Used Prior to application of this unit, the patient should not have an active bleeding at the site of surgery to give a chance for proper application of the unit.

First, when a patient is in supine position, the wrap, covered by the inner wrap, is placed under the patient in an appropriate position.

Second, the inner wrap is wrapped around the patient, and the place where the balloons will be placed is chosen.

Third, the balloons are placed on the appropriate positions. A layer of glue on the outer surface of the inner wrap may be used to hold the balloon in place reasonably secure.

Fourth, the ends of the lower straps or wraps are brought together and tightened to hold the balloon in place. Then the ends of the upper straps or wraps are tightened together. The balloons may be inflated to some degree prior to this stage to make the positioning easier.

Fifth, the balloons are inflated further to provide the desired pressure. At this stage their pressure may be checked and then the openings of the balloon closed. Then the patient is asked to move and sit on a chair and report if there is any problem. A measuring gauge and an inflator bulb or a syringe are provided to patients with explanation of how to use them if they happen to be needed and the telephone number to call if they have problems or questions.

This unit is applied in the hospital or clinic prior to discharge of the patient or when patient is being moved out of the bed.

I believe the use of this unit has the following distinct advantages:

1. Most importantly it is the best available way to prevent bleeding and complications in the intervention area. The protection will give the most and best peace of mind to the patient, their relatives, and the physicians.

2. It will prevent or diminish the complication in the area. I believe that many times the damage to the artery and the area is small and will not be detected or even when noted. Nothing really can be done or will be done about them due to the limitation of present techniques. However even if small, they are still bad, and the patients will suffer to one degree or another. This should be avoided by use of these units.

3. When the protection of the patient from bleeding can be continued by these units, then the patients can be discharged earlier from hospital and this has the great advantage to diminish the need for very skilled medical personnel to stay longer and to give longer care to these patients. This will diminish the cost and may pay for these units many times.

4. This will allow early discharge of the patient and it is good for the patient and his family. Some can be released during day time rather that being kept until dark. It may also help a patient to return to the job earlier.

5. The need for use of heavy adhesive taping and Tin co bin and gauzes will be practically eliminated, and this will also help the unit to be paid off.

6. When the use of adhesive tapes and Tin co bin is drastically diminished, then it will decrease the related allergic reaction and skin discomfort as well.

7. It is important to notice that the fact that the pressure inside the balloon can be changed by this given method gives is big, useful option, since the need for pressure can change due to different physical and pathological conditions of a patient (even in one case itself). For example the level of blood pressure of patient makes a big difference, or if a condition with cough develops that increases the need for more protection, or the weight of a patient and their body built, etc.

The Detailed Explanations of the Figures

Figure 33:
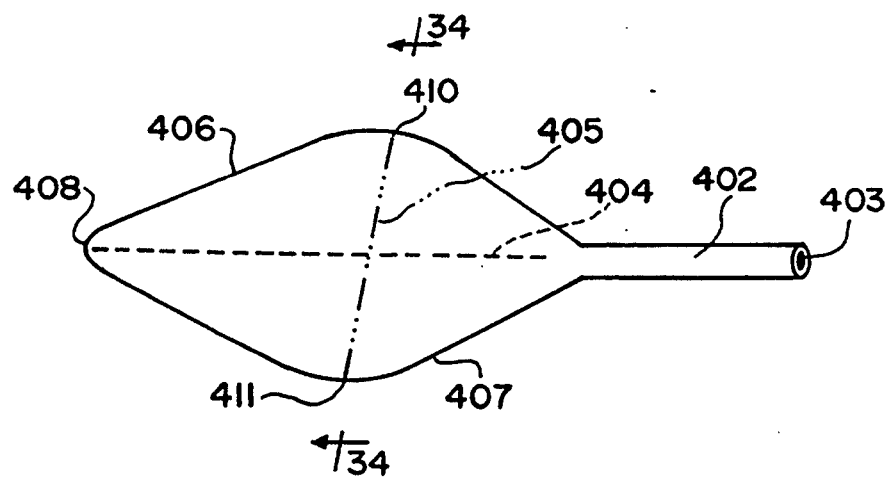
FIG. 33 is a plan view of another balloon.
Figure 34:
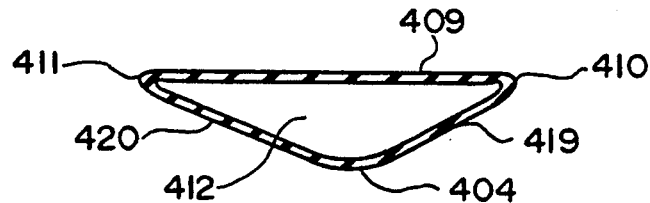
FIG. 34 is a transverse cross section as taken along line 34—34 in FIG. 33.

FIGS. 33 and 34 show a balloon having an inflation tube 402 at the right side. Its tip is 403, and the tip of the balloon at the left is 408. The almost horizontal line 404 shows the location of the vertex. A dot-dash line 405 is to illustrate the short axis, or the shorter diagonal, of this balloon. The upper tip of this shorter diagonal is shown by 410 which will be placed on the lower abdomen area. The lower tip 411 is placed on the thigh area. The upper border 406 is placed on the lower abdomen area, and the lower border 407 is placed on the upper groin area. It is intended to make the short axis 405 stand over the main artery of the lower abdomen and groin so it may be a little more oblique in some cases. The straight upper rim is 409. The slightly curved line 419 is showing the surface that will stand on the lower abdomen skin. The line 420 shows the surface that will stand on the upper groin area. 412 is the inside of the balloon.

Figure 35:
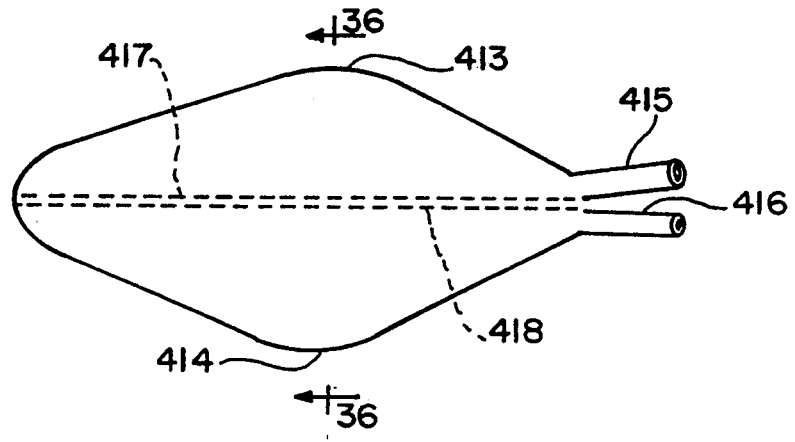
FIG. 35 is a plan view of another balloon.
Figure 36:
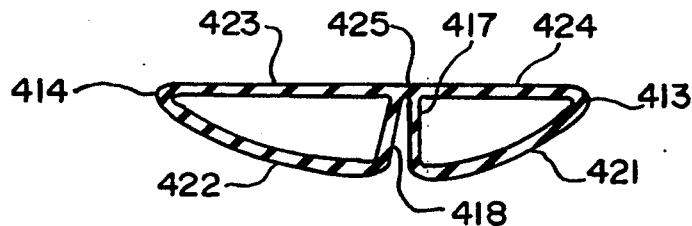
FIG. 36 is a transverse cross section as taken along line 36—36 in FIG. 35.

FIGS. 35 and 36 show another balloon which is made from a combination of two balloons. There are two inflation ports 415 and 416, one for each balloon. Here the dotted line 417 shows the lower border of the upper balloon, and the dotted line 418 shows the upper border of the lower balloon. The narrow space between these two lines is the connecting piece. The upper tip of the upper balloon is shown by 413, and the lower tip of the lower balloon by 414. In general, the overall shape of front view of these two balloons together looks like the balloon shown in FIG. 33. 424 shows the top surface of the upper balloon, and 423 shows the top surface of the lower balloon. These two balloons are connected to each other along a line shown by 425. The upper surface 421 will stand on the lower abdomen area, and the lower surface 422 will stand on the upper groin area.

Figure 37:
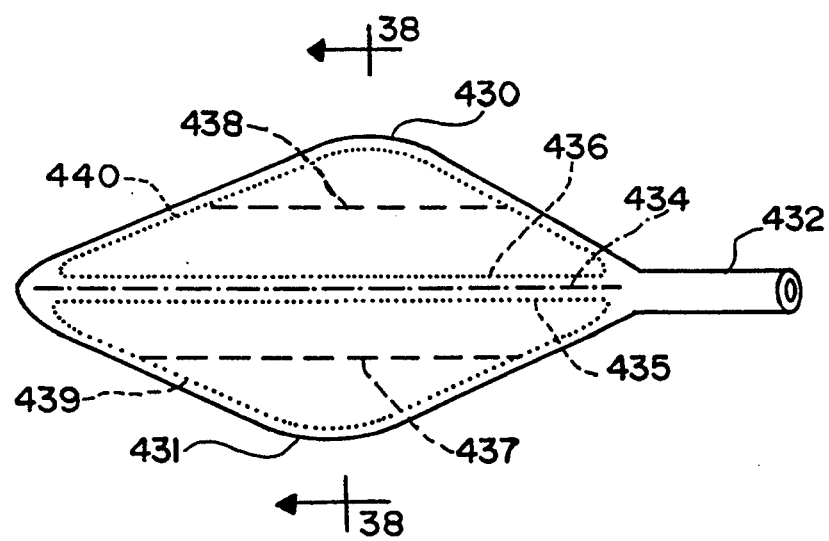
FIG. 37 is a plan view of another balloon.
Figure 38:
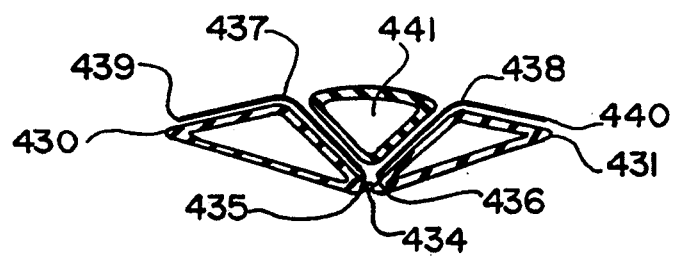
FIG. 38 is a transverse cross section as taken along line 38—38 in FIG. 37, and showing a further balloon.
Figure 39:
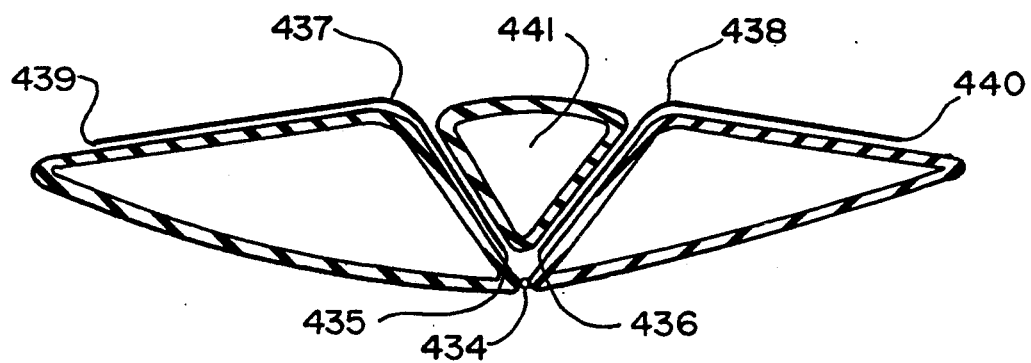
FIG. 39 is an enlargement of FIG. 38.

FIGS. 37-39 show another model made from a combination of two balloons, but having a hard plastic or rubber or thicker latex cover on its surface and also fortified by the pressure from a third balloon. FIG. 37 shows only one inflation port 432 to indicate the possibility that one port may be chosen for inflation of two balloons. The tip 430 in the top and 431 in the bottom are shown. The dash-dot line 434 indicates the connection line between these two balloons. The two almost triangular shapes, one on the top and one in the bottom, with dotted line borders 440, 436 for the upper and 439, 435 for the lower are thick plastic pieces that stand over these balloons to allow the person to bend his hip without distortion of the pressure in the balloons and the shape. The dashed lines 438 and 437 show the vertex of these two plastic pieces. One tip 431 is on the right side, and the other tip 430 on the left. Numerals 440, 438, and 436 show the hard plastic that stands on the upper surface of the upper balloon. Numerals 439, 437, and 435 show the hard plastic that stands on the upper surface of the lower balloon. The connection 434 stands against the groin line. The third balloon shown by 441 is to fit the space between these two balloons and to press the center.

Figure 40:
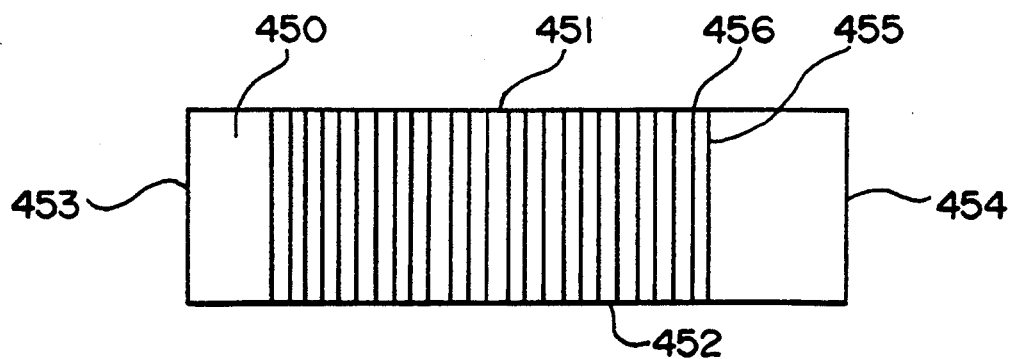
FIG. 40 is a plan view of a latex layer having an accordion-like zone that allows a certain amount of stretch.
Figure 41:
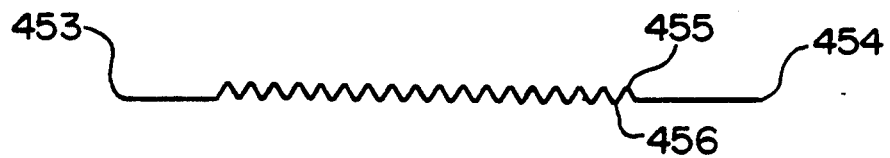
FIG. 41 is a front edge view of FIG. 40.

FIGS. 40 and 41 show a thin rectangular latex layer that has a zig-zag area along its length. The borders are 451, 452, 453, 454. In the center, parallel lines 455 and 456 are to show the ups and downs of the zig-zag construction. This zig-zag area may be referred to as an accordion since it allows the layer of latex to be pulled and have its length increase.

Figure 42:
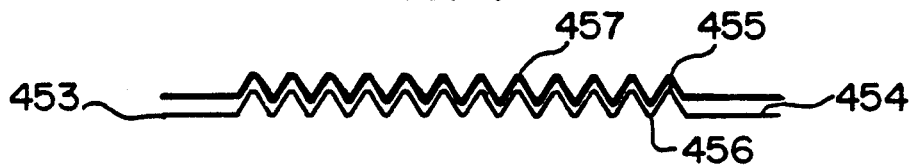
FIG. 42 is a view like FIG. 41, but with a modification.

FIG. 42 shows a latex layer similar to the one shown in FIG. 41, except this unit has a lining 457 of soft stretchable fabric on its face.

Figure 43:
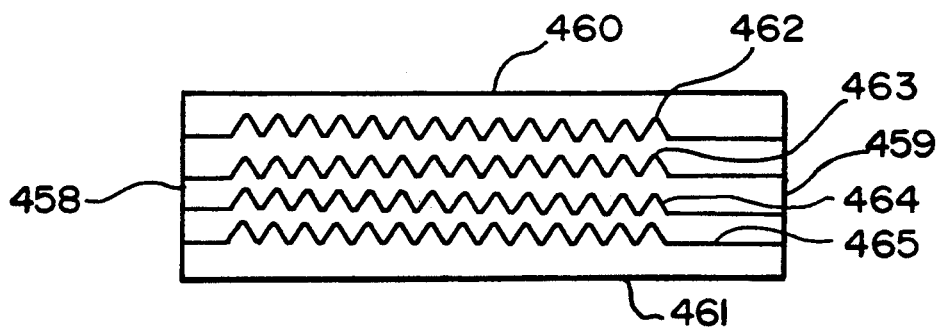
FIG. 43 shows the front view of a rectangular latex layer that is flat but has a series of parallel lines of non-stretchable fibers or metal that will function as a means of controlling the ultimate length of this piece when this layer is pulled.
Figure 44:
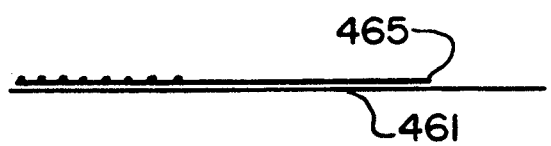
FIG. 44 shows a front edge view of the latex layer shown in FIG. 43.

FIGS. 43 and 44 show a thin rectangular latex layer that is flat, but has a series of parallel lines of non-stretchable fibers or metal that will function as a means for controlling the ultimate length of this piece when this layer is pulled lengthwise. In the center of this layer, the zig-zag shape of these fibers is shown. The borders of the layer are shown by 458, 459, 460, and 461. In the center, parallel lines 462, 463, 464, and 465 are shown with their zig-zag construction in the center.

Figure 45:
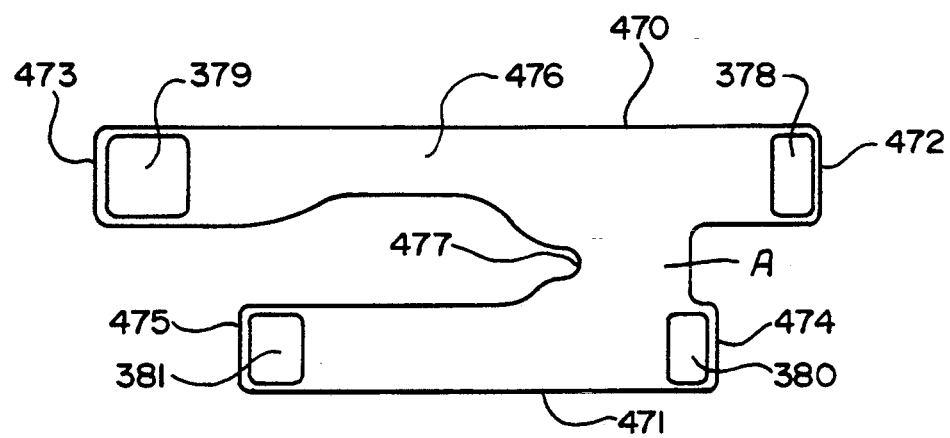
FIG. 45 shows the front view of a latex support unit that is to be wrapped around the upper waist and the upper thigh area.

FIG. 45 shows a latex support unit that is to be wrapped around the upper waist and the upper thigh area. This is a general shape that more or less will be shared basically between the latex layer itself and the inner liner and the outer non-stretchable support unit as well. This unit has an upper part that will wrap around the waist and upper groin to give support to the balloon in the upper groin/lower abdomen area. This part will be held in place by having its end pieces 472 and 473 come and be stuck to each other by use of patches of contact, such as adhesive surface, Velcro TM patches wherein one of the Velcro TM patches will be placed one on one surface of this cover and the other on the opposite surface of this cover, or snaps, etc. The upper border of this part is shown by 470 and the area that will stand on the lower spine area is marked by 476. The lower part of this unit has a lower border 471 and this piece will be wrapped around the thigh area (commonly the right side since it is used most), and it will be held in place tight and securely by having its end pieces 474 and 475 come and be stuck to each other by use of similar means to those described for 472, 473. The common area in between these upper and lower parts has an angle shown by 477. The area A adjacent to this angle area will stand over the groin line and has the job of supporting the balloon in place. The dome shaping of this cover to fit the convex areas of the body is not shown in this FIG.; however it is mentioned in the text.

Figures 46, 47:
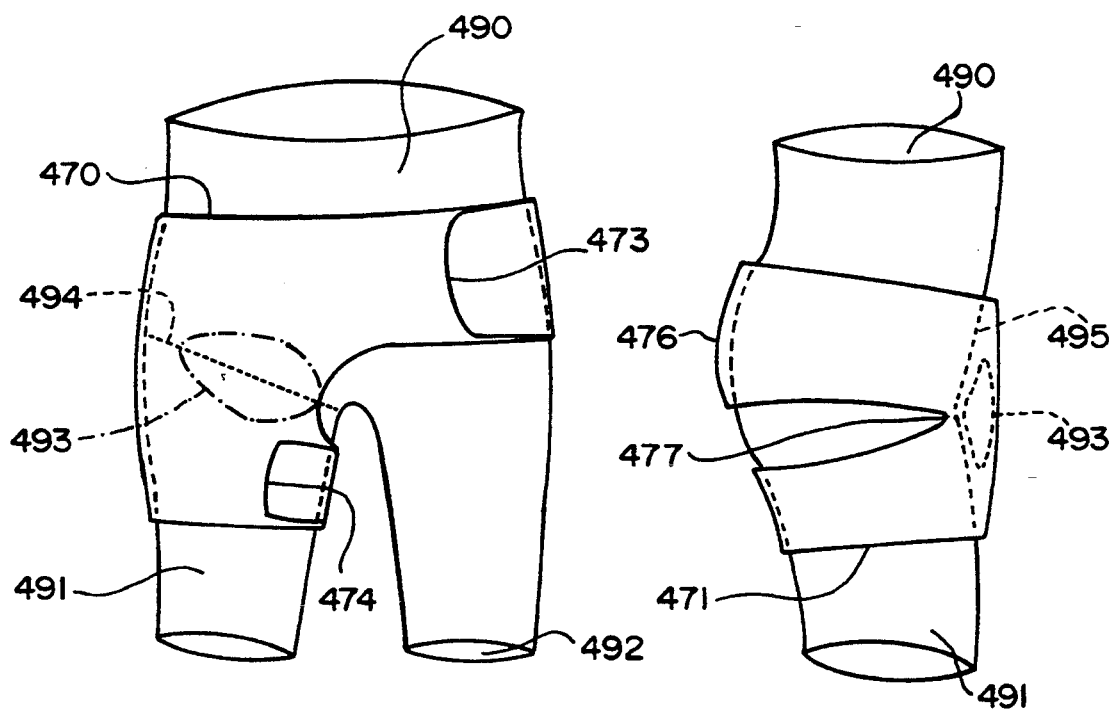
FIG. 46 shows a patient wearing the support unit shown in FIG. 45.
FIG. 47 shows the right side view of the patient in FIG. 46.

FIGS. 46 and 47 show a patient wearing the support unit shown in FIG. 45. This shows the general placement of this unit on the body and how the upper part of this unit is wrapped on the waist area, and the lower piece around the upper thigh area, with their end pieces coming over the surface of the other end to keep the unit in place securely. The groin line is shown by the dotted line 494, and the approximate position of the balloon by dot and dash line 493. The trunk of the body is 490, the right thigh is 491, and the left thigh is 492. FIG. 47 shows the open area between these two pieces in the back and in the side of the upper thigh ending with vertex 477. This is an important element of this design that allows the patient to be able to sit on a chair and bend his hip joint. The front of the lower abdomen under this cover is shown by dotted line 495, and the balloon in front of the groin line with its vertex right on the groin line is shown by 493.

Figure 48:
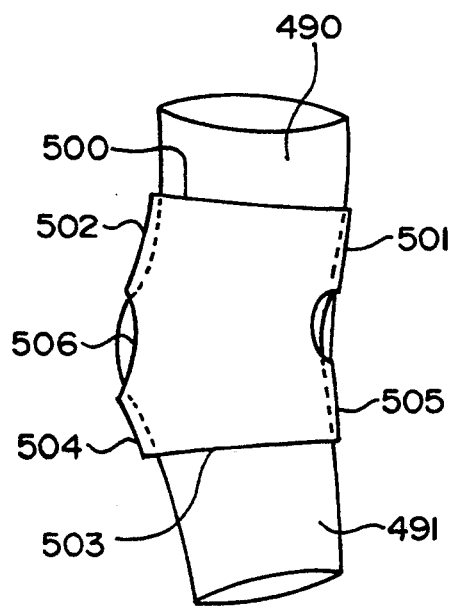
FIG. 48 shows the right side view of a patient wearing a support unit that has a shape similar to shorts.
Figure 49:
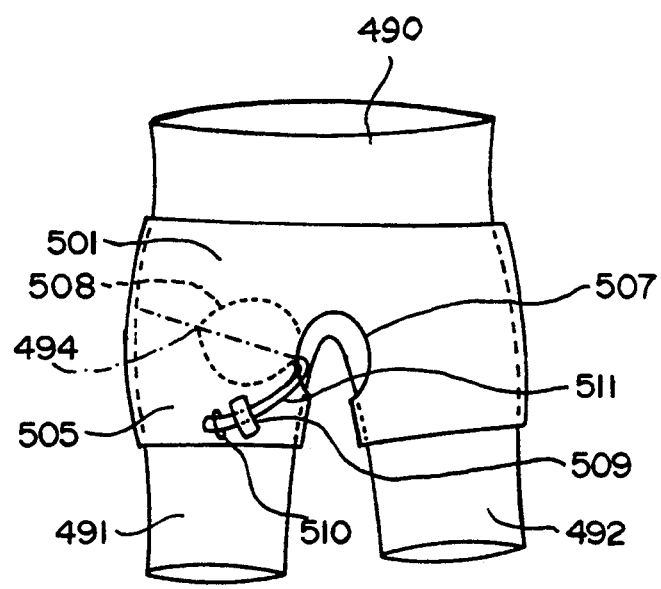
FIG. 49 shows the front view of the patient in FIG. 48.
Figure 50:
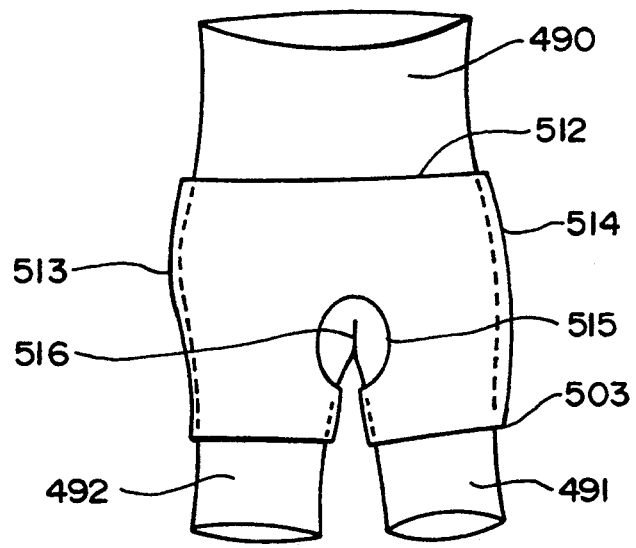
FIG. 50 shows the rear view of the patient in FIG. 48.

FIGS. 48-50 show a patient wearing a support unit that has a shape similar to shorts, except it has openings in front and back. The front opening is in front of the genital area, and the back opening is in front of the anal area. These Figs. show the general size of this support cover and the way it holds the balloon reasonably sturdy in place. The upper rim of this support is shown by 500, the lower rim by 503, the upper rear surface in the belt area by 502, the front part of it by 501, the lower rear surface in the back of thigh by 504, and the front part in this area by 505. The trunk of the body is 490, and the right thigh is 491. The border of the opening in front is shown by 507, the groin line by 494, and the balloon by 508. The inflation port of the balloon is shown by 511, and comes and is held under a Velcro TM patch 509. The tip of the inflation port has a three-way stopcock shown by 510. The border of the opening in the back is shown by 515 and the line between the buttocks by 516. The upper rim of the support cover is 512, the left side of this cover is 513, the right side is 514.

The further improvement invention that is introduced in this application (and which I call D.Device 3) deals with making an inner unit which is intended to be much more comfortable for the patient and to achieve a better goal in this regard. The application of this unit is easier. A unit that can be used in a larger group of patients makes its final cost cheaper as well.

For such purposes a layer of latex is chosen for making the basic structure of these units. Making this unit from latex gives the following advantages:

1. The unit will have the capability of accepting the shape of the underlying body.

2. The unit will be elastic and can stay in place nicely without causing much discomfort. Also it can apply some force to the underlying balloon to keep it in place securely until further support is provided.

3. The unit can be cut to sizes.

4. The wall of the unit will allow non-stretchable adhesive tapes to be applied to it for controlling its length.

5. The thickness of the wall of the unit can be different in different areas and spots to control the strength as well as elasticity selectively.

6. The unit can be made to be sterile.

7. The unit can be made to be reasonably cheap and affordable.

8. The unit will have the option of preventing moisture from contaminating the area.

9. The unit can be made to have openings to allow sweat to pass through.

10. The unit can be reasonably made in desired and different shapes.

11. The unit will be non-toxic and does not have bad odor.

Having these factors in mind then, a specially shaped latex layer has an upper part to go around the waist area and another part to go around the upper thigh area that come and are wrapped around to hold one or more pressurized balloons in place. Although this piece can be used alone in certain circumstances, it may be made to also have an inner liner piece made from a soft, absorbent, stretchable, likeable layer such as a fabric made from cotton or similar natural or synthetic material. This inner soft layer is to give a good feeling and to stay in place nicely and also to absorb small amounts of sweat and some secretions, blood, etc., that may stay on the skin even after cleaning. This layer may be sterile and will be connected to the inner surface of the latex loosely, to allow the combination to be stretched. They are connected to each other either by spots of glue or by being sewed or by similar means.

A latex layer is chosen to cover this unit and to have its own shape to allow it to be lengthened as desired. This will happen by having pieces in the wall similar to the wall of an accordion that will allow the unit to be pulled to provide more length to the layer without being weakened or overstretched. The ends of the upper and lower pieces of this piece will be connected to each other strongly by use of one method or another, such as adhesives, snaps, or adhesive tapes. To make the connection tight and strong, the end pieces of this unit may also go under a matching plastic band or bridge then to make a U turn to come and stick on the rear surface of its own. In most models the rear surface of the balloon will have an adhesive surface protected by a plastic cover that will be removed to allow the balloon to stick to the inner surface of this cover. In some models the plastic cover may have end pieces that can be held together by going over spores of a hard plastic that will allow the holes on the latex cover to fit on them and be held in place this will be similar to the belt and the buckle of the belt, importantly the other end or ends of the latex may also come and be held by similar spores in place. In such cases the latex cover will have holes in its ends for such function, with stronger surroundings around the hole of the spot.

Importantly a layer of non-stretchable material can be stuck onto the latex to allow control of the length of the unit to be achieved. Also it will allow some previously designed tapes of non-stretchable materials to be removed to allow the length of the unit to be longer. In order to allow the ends to stick better, the ends of this cover will not have the fabric cover.

Also the latex layer may have areas or patches of openings in its surface as previously designed. However, it may also have designs and shapes on its surface that will allow some other areas also to be cut if so desired; for example in the case of using the balloons having hard plastic covers (to be explained later) the area of the latex cover which will stay on the area in between the plastic covers may be cut open to allow better functioning. Also in the sides of the hips it may be desired to cut the unit open for better ventilation and evaporation and in some other spots or areas such cuts may be desired as well. It may be mentioned here that the extra length of the latex can be cut short to make it customized to fit nicely and avoid useless extensions to stay.

Also importantly a special layer of latex will be made and utilized in the construction of such a unit (this layer is here referred as D.Latex) will be made from a layer of latex or a similar elastic material that will have lines of fortification and supplement of lines of non-stretchable fibers in a sense similar to dental floss or a soft thin metal wire or something similar so that these fibers will be soft and bendable however to resist the stretch. Importantly these lines may be incorporated in a zig-zag form and also the latex layer may be in a shape similar to the wall of an accordion so the combination of this latex and such fortification fibers will allow certain degrees of stretch of the latex to be achieved until the fibers reach their full length-or the predicted limitations and then the fibers will prevent further stretch.

Some areas of the latex may be made thicker to give more protection or shape needed. The thickened area or lines may function as areas or lines or shapes of fortification as well.

The use of this latex unit which is fortified by one method or another as mentioned, may be enough in some cases to allow a unit to be made that would not need another non-stretchable support. This will be very important in cutting cost.

Naturally these important factors will be considered and calculations of the length and make-up of this unit will be done meticulously so that after the wrapping of the unit, the stretch of the areas will be allowed in certain directions as planned. For example the areas of the cover in the buttock areas will allow the unit to stretch in head to toe direction when the hip is bent. However it will not allow the cover to turn loose since the fibers in the buttock area that are in transverse direction will not allow the length to increase.

Importantly the latex support unit can be also made in the shape of tight shorts covered by soft lining as mentioned so that at the time of release from a hospital or clinic, a patient could wear them easily and have the balloons placed under it securely as well. Further protection of such latex covers will be provided by use of adjustable well-designed, non-stretchable shorts to be worn over the latex cover in order to function as a support unit for the balloons. It is not meant that the whole shorts will be non-stretchable; however, it is that bands or straps or pieces of non-stretchable material will be properly incorporated in the lower abdomen and upper thigh area of such fashionable shorts so that they will allow the proper and necessary protection of the balloon to be done. These pieces will be adjustable to be used comfortably. I believe that with proper tailoring and designs such units can be made to look nice and fashionable and be comfortable and likeable as well, so that overall the use is made much more convenient and continuation of the application of pressure practical. In summer, patients may be able to leave the hospital with those units worn very much like regular shorts with a new fashion. In winter, the units have less outside extras and thickness to allow them to be worn under the slacks with comfort.

In general the latex unit will have openings in front of the genital area going and extending to the back and anal area, to allow as comfortable use of such units as possible, plus sitting and urination and defecation to occur without a need for the unit to be removed. In some models of such units, the units may have extra space and loose wall cover in the genital area to prevent pressure to the genital area which could be very bothersome especially in men. These shorts will also have a pocket to hold the inflation device in place or to have bands of Velcro TM in order to hold the inflation tube and to hold the inflation device to make this job more convenient.

It should be considered importantly that if there was a difference in the size of the latex then it can be adjusted by the use of techniques predicted here: such as if the length is short the walls can be released and if the length is longer than desired then bands and tapes of non-stretchable adhesive tapes can be applied on the surface of the latex to make it fit desirably.

Also models can be made to have an opening and a window in front of the cover of the balloon in order to allow the wound area to be checked easily and the balloon to be exchanged if needed. The sides of this window to be closed with use of a cover and related appropriate supports, and to be tightened by presently available methods by using Velcro TM patches or snaps, etc. Technically in order to make the connections tight, one end of this window cover can be sewed to the cover and the other end pieces of this unit may go under a matching plastic band or bridge then to make a U turn to come and stick on the rear surface of its own.

The Shape and Structure of the Balloons

This unit uses a special balloon made from rubber or latex or similar material to look like a modified rhomboid for the reason that the diagonal lines of it will not be perpendicular to each other as is clearly shown in FIG. 33. The oblique diagonal extension of the balloon in the direction of the large vessels in the groin is intentional to allow the pressure in the wounded vessels and its vicinity to occur with enough protection and to prevent bleeding in that area. The size of the balloon is also intentionally much larger than the width of the vessels in the area. The reasons for this are many, such as follows:

1. The fact is that not all the time the site of entrance into the artery is exactly on the very front wall of the artery. Since this entrance happens blindly it is very possible that the site of perforation will be at the side of the front wall, even at times in the very side of the arterial wall. These are the cases where pressure to the wall of the artery in front is not as effective for prevention of bleeding and hematoma since the pressure is not applied at the bleeding site. Therefore I believe in such cases the pressure to the artery and adjacent area will be more effective in prevention of oozing blood than the direct pressure over the arterial wall itself.

2. When the vein is also punctured (which many times happens) the pressure over the vein will be also desirable and beneficial to prevent bleeding from the vein, especially when the pressure inside the vein happened to be high in certain cases such as pulmonary hypertension when the pressure on the right side is also very high.

3. It is also observed by myself in practice that in a good number of cases the ecchymosis after such procedures extend more than the entrance spot to the vessels, and it is in fact an area rather than a small spot such as needle point. Therefore it has given me the indication that the protection is better if larger than the wounded small spot of the skin.

4. It is also believed by myself that providing a pressure to the area will be more effective in prevention of pseudoaneurysm and this can be best done by such balloons that cover more than the needle entrance area.

Please be notified that the shorter axis or diagonal line of this balloon is chosen to be oblique due to the fact that the large arteries in the groin area come in oblique fashion and therefore it is intended to have the shorter axis of this balloon to match that direction of the large vessels in that area and directly and precisely to stay on top of them as accurately as possible. So protection of the potentially wounded areas have been intentionally considered in choosing such a shape.

From the other side this balloon will have a raised surface in the face against the groin when inflated. This will be like having a vertex that has a line almost along the long axis or long diagonal of the balloon to fit the groin line similar to one mentioned in my first application. This is to divide that surface to an abdominal surface and an upper thigh surface. The abdominal surface will stand and confront the lower front abdomen over the large vessel and next to the groin line. The surface for the upper thigh area will stand on the great vessels of this area next to groin line.

The rear surface of this balloon will be flat having a layer of adhesive protected by removable plastic layer or to allow the adhesives to be stuck on it. This allows this balloon to be independently chosen according to the size of the patient, and secondly the location of this balloon compared to the inner surface of the cover can be easily and selectively adjusted and chosen. This balloon is placed to face the wound area. The front surface of this balloon is sterile or covered by a sterile cover or sterile gauze pad stuck on it. This gauze pad may have a plastic base to prevent wet and contaminated materials and secretions from going through it. So importantly again the special shape of this balloon when modified and made in different sizes will give the important freedom of using it in different people with different body size as well as different amount of fat in the groin area. It should be considered that there are different people with totally different sizes and with different anatomy in the groin area as well, and although many have a rather small amount of fat in that area, however there are others that have a very large amount of fat in the area both originating from bottom of their abdomen and from significant deposit in the upper thigh area. Also the anatomy of the whole area is quite different when we consider a large group of people as a sample. So the need for use of different size balloons is real and such different choices will be then very useful to allow an appropriate balloon to be chosen to stand on the groin line and allow the appropriate pressure to be applied in the desired spot and to let this function to occur in those different cases. The balloon for the upper groin may be different than the balloon for the inner groin area. Their shape and size and inflation ports may differ. Utilizing such balloons will allow the balloon for the lower abdomen to be separately chosen from the balloon for the upper thigh area. A third balloon previously introduced may be used to go over those two balloons as well, to intensify the application of force in that area as required. What it is predicted and I will also claim in this application is that to have a balloon that will cover the upper groin area over the invasion site with a shape to cover the area intended to be protected. This balloon will have an upper line which is almost a straight line to stand on groin line then the balloon to have another curved line that will be something like a half circle or similar shape with an axis to stand over the groin vessels for protection of that vessel. The thickness of the inflated balloon in the groin line area will be higher than its curved edge, this it to match the anatomy of the area. Since in general the groin line is lower than surface of the lower abdomen and the upper thigh surface connecting to it, also the need for application of pressure is more close to groin line than the periphery. The same construction will be almost true about the second unit that is to stand on the lower abdomen area and in this case the balloon will have a straight line to stand parallel and adjacent to the groin line and a curved edge in the other side similar to part of an oval shape with an axis to stand on the big vessels on the lower abdomen which it will be covering. These two pieces may be connected to each other by a piece of latex or an adhesive tape. In certain cases they may be chosen independently to match that groin area of a given patient. The inflation ports may be connected in some cases, but in general they will be separate to allow different level of inflation of occur.

Also importantly some models of balloons may be made with a hard plastic cover in their rear surface in order to give support to the balloon and help in shaping the outside of the balloons in special ways. For example one distinct way of use of such balloons will be a two piece balloon with specially designed rear surface that will allow the person to bend his or her hip joint to sit on the chair without having a significant disruption of such balloons function. In this case the plastic cover will be made from hard plastic with an angulation in its surface of about 135 degrees or so to allow such function to occur as shown in FIGS. 38 and 39. In these cases this plastic is bent to have an angle. Then the third balloon will be inflated and press on the center part of those two first balloons to apply enough pressure on them and have them functional, supplying heavy pressure at least in the early stage of prevention from bleeding when the need for hemostasis is high and many patients have potent blood thinners in their system which is not metabolized and disintegrated yet. As mentioned earlier, the rear surface of these plastic covers may have an adhesive surface protected removably by a plastic cover that will be pulled to allow these balloons to stick to the inner surface of the supportive cover. Alternatively it is possible to have a thick layer of latex or rubber to cover the rear surface of the balloon instead of the hard plastic. This construction may in practice do the same job as the hard plastic, but be somewhat softer and better tolerated.

The connection of the third balloon to the outer layer will be made to be easily releasable so that connection and disconnection of the third balloon is easy enough to give the chance of undoing it when is not needed (when the patient has to sit up and to connect by a Velcro TM patch when patient has to lay down). In one technique of doing it the cover or the third balloon may be sticked to its rear surface. In order to make the connections tight the end pieces of this unit may go under a matching plastic band or bridge then to make a U turn to come and stick on the rear surface of its own which is a common technique used.

It is to be mentioned here that there will be different models of balloons available for the user for the reasons that:

A. The people's size are different, and their need for a different unit is natural.

B. The anatomy of the groin area between people of the same weight may differ significantly due to the height, muscle size and fat size, gender difference, etc.

C. Even in a given size the size and shape of balloon may need to be chosen different when the extent of work-up is different. Consider cases that patient had uncomplicated cardiac catheterization without need for venous line, as well as potent blood thinners, this is different than the cases that angioplasty was done, a larger sheath was utilized and inserted inside the artery for a long time, also the vein was canalized and potent blood thinners were utilized, also consider if intra-Aortic balloon counterpulsation was used which needs much bigger sheath to be inserted to the artery, which all of those indicate a need for a stronger, better and longer control of bleeding and blood oozing to be done. Therefore the need is much more and choices should be provided. For this reason first of all it should be considered that the following changes are predicted:

First, the length of the balloons in the groin lines may be chosen to be different to match the different sizes.

Second, the thickness of the balloon may be chosen different, to match the anatomy of the place.

Third, the size of the balloon along the shorter axis to be different to match the need due to different level of intervention.

Fourth, the connection between two balloons in models that two balloons are used is not permanent and can be easily cut, and they can be easily connected in the site and distance which is decided to be the best by application of adhesive tapes and the connection can also be cut and different balloons can be chosen to match the needs.

Fifth, the degree of the curves in the surface of the balloons may be chosen to be different as well.

It is also possible that in some cases modified balloons filled with jelly-type feeling such as silicon jelly to be used instead of air filled balloons.

The Outer Non-Stretchable Layer

In general and in models where the latex layer is not fortified there is a need for a higher protection of the inner cover and to give a support for the pressurized balloon to press against the body surface. This will be provided by use of a wrap made from a layer of non-stretchable material that is to keep the inner cover in place and also to give enough support for the inflated balloon. This non-stretchable piece or cover will have a general shape similar to the inner cover except will be somewhat larger to go over the inner cover.

I would like to add that it may be better to do some skilled tailoring to make some doming of the cover over some areas such as the buttocks, as well as some over the balloon, in order for the unit to stay in place comfortably and securely and to hold the balloon in place as well. The outer surface of this cover may have a pocket and bands of Velcro TM in order to hold the inflation syringe or pump and the continuation of the inflation tube and threeway stopcock in place conveniently.

This wrap will be made from the following different materials:

A. From a non-stretchable material such as woven fabrics that are used to make the body of some commonly used school bags. Importantly in some models of such cover, the rear part of the unit will have a cut or open space to allow the patient's hip to bend easily. The front ends of this unit will come together to be held by Velcro TM patches or other kinds of snaps or connections. In order to make the connections tight, the end pieces of this unit may go under a matching plastic band or bridge, then make a U turn to come and stick on the rear surface of its own.

B. Importantly the outer layer may be also made from a net or screen made from non-stretchable material similar to those commonly used for packing fruits and potatoes. The ends of these covers can be pulled to come and go over a line of hooks on a plastic like a buckle. Naturally for this purpose these units will be made with much higher quality to be deluxe and to hold the latex nicely. This design is important since it will allow the person to bend his or her hip without much problem. The ends of this unit may also be held by Velcro TM patches or other kinds of snaps or connections.

C. The latex layer itself may also be covered by an adhesive tape made from a non-stretchable material that when in place will cover the surface of the latex layer to prevent the unit from being stretched further.

D. Importantly the D.Latex may be also used for this purpose. In this case the layer of latex or a similar elastic material will have lines or threads or bands of fortification with use of non-stretchable fibers. That may be exampled by thick dental floss fibers, or a metal fiber or similar material, so that these fibers will be soft and bendable however will resist the stretch whenever their full length has been met. These fibers will be incorporated in a zig-zag form on the latex layer, or these fibers can be incorporated in a latex layer that has a construction in the shape of the wall of an accordion so that combinations of the latex and such fibers will allow a certain degree of stretch of the latex layer to be achieved until the fibers reach their full length and then the fibers prevent further stretch in their direction. However when the fibers are also laid in the other direction that is perpendicular to the first fibers then there will also be another series of non-stretchable fabrics that will show their own function to prevent stretch of the fibers in that direction. The combinations of these two groups perpendicular to each other will allow a unit to be made that is a very useful unit for this purpose, so that in practice and when properly designed it will prevent stretch of the unit in hip to hip direction but to allow the stretch to occur in head to toe direction in the back and allow the patient to be able to bend his hip when wanted. The importance of such construction is that in some models it will eliminate the need for outer support cover since this latex layer will be strong enough to perform the job of support alone with having the inner cover of absorbent material as well, in order to have absorption of the perspiration to happen. When it is desired such as in high temperature, etc., the latex may have openings in its surface for changes of the air to occur. It should be considered that one advantage of the latex is that it will allow windows to be cut when needed, also tapes to be sticked on it.

Importantly I would like to mention that with proper planning the balloon and its covers can be made from transparent, clear available materials to allow the wound area to be observed for possible bleeding.

Safety Techniques

A couple of safety systems are thought to be useful in making these units safer and they are as follows:

1. The equalization system: Importantly in order to prevent sudden change in pressure of the balloon from causing a problem, for example when the patient sits up and bends his hip, these balloons may be connected by a tube and to another balloon (with use of a threeway stopcock) that is outside of the cover so that when the pressure of the inner balloon increases significantly due to bending the hip, then the air escapes into the outside balloon, to return when the pressure is lower. The outside balloon may be kept inside a tight cylindrical chamber facing a flat surface in front of an adjustable spring similar to one mentioned in alarm part of D.Device so that the amount of pressure to the balloon can be adjusted. The higher pressure formation inside the groin balloon will push the air into the outside balloon and the expansion of that balloon will push the spring backward and when the pressure inside the groin balloon is lowered then the spring will push the outside balloon back and air will come inside the groin balloon, and a buffer action can continue.

2. The alarm and monitoring system will be used in order to set the pressure in desired level and to control it, the balloon can be connected to an electronic device as well as an alarm unit to prevent from under- or overpressurization of the balloon to occur, and also to give warning if significant changes occurred in this regard.

3. The patient will be provided with a small mirror that can be sticked to the outer surface of the shorts so that the patient can raise it and check the groin to see if there is bleeding in the area.

4. I have indicated previously in D.Device about a hydrophilic mesh which stays inside a tube that will carry blood outside if it occurs.

5. In some cases the balloon of the unit can be connected to an automatic pressure control system to prevent a drop in pressure of the balloon and inflate it if needed. This can be of significant importance in patients that have a fluctuating blood pressure, rising very significantly in such cases or even dropping much. These are not good for the patient and we do not want to press the groin vessels more or less than needed and appropriate. The pressure inside the balloon of the groin can be electronically checked and adjusted to stay some numbers above the femoral artery or systemic pressure of the patient based on the physician's decision.

6. Educational video tape will be also provided to patients prior to their discharge to teach them how to react if unexpected bleeding occurs. Extra balloons will be given to them and special teaching will be provided to make this job safer and also to give patients much more peace of mind and comfort than today. Giving safety and comfort and peace of mind is something that I want to make a positive impact on them.

The Value and Some of the Advantages of Use of This Unit

This unit will be of extreme value in prevention of bleeding in the intervention sites and will be of great help in such patients. Some of these benefits may be mentioned as follows:

1. First of all this unit is the most effective unit for such uses and that is the most important thing.

2. This unit will practically eliminate the heavy use of adhesive tape and chemicals such as Tin co bin and will help to reduce patients' pain and bad reactions in this regard and so will cut the cost as well.

3. The system will allow patient to sit earlier and even to stand up and move earlier and faster and not to suffer with staying immobile on the bed. Many of these patients suffer from back pain and other problems and staying in bed is the last thing in the world they want to do.

4. The fact that the balloon can be changed easily is of great value, and special unique uses are also possible; for example, if the patient developed hematoma in the groin and the physician wished to use cold compress in the area, this can be easily done by filling the special balloon with iced water and placing it on the wound area to provide the pressure as well. Even in later stages a warm compress may be applied by the same technique if wanted.

5. This unit due to its inherent protection and safety will allow the patient to be discharged home earlier and this has many benefits for patients as well as medical staff. The fact that a patient can be sent home early prevents driving long distances especially in winter in dark on slippery roads, since not all the cases start and finish in the morning. The fact that the need for medical supervision will be less will diminish the cost to pay for the unit many times.

6. This unit has its own value in preventing anxiety and fear of the patients as well. It will allow a patient to cough, raise head of the bed, and even sit up much earlier without having fear of causing damage. This unit or different models of it can be kept in place for a longer period even during and after discharge from the hospital to provide physical and psychological security to patients and will allow them to feel secure and comfortable. This will cause patients to start their normal life earlier and return to their job in many cases again to have its good financial effect.

Since the bleeding will stop if the local pressure is higher than the blood pressure of the patient in that area, then this provides a means that a patient can use the inflator unit if needed to control the bleeding and so be safe and have the chance to contact medical staff.

7. Importantly the appropriate size unit can be chosen prior to procedure so that it can be spread on the procedure table prior to procedure and to be rolled on the sides so that after procedure there will be no need to move patient for wrapping this unit and the lines can be pulled on the table right away by the medical staff and the pressure will be applied and the patient then can be moved out in the early stage. The pressure inside the balloon may be little higher and then decreased and decided. Such a technique will eliminate the movement of the patient for placement of such unit and overall will diminish moving a sore and uncomfortable patient and the total job noticeably.

8. Importantly this unit with only minimal modification can also be very useful in patients with inguinal hernia or after hernia operations, even in the case of many similar surgeries such as intra-abdominal surgeries.

What is claimed is:

1. A wrap for holding a pressure-applying means against a person's groin so that pressure can be exerted by such pressure-applying means against the groin, yet allowing a person to both sit up and lie down while pressure of such pressure-applying means continues to be exerted on the groin, said wrap comprising an abdomen-wrap portion for encircling the abdomen proximate the groin and a thigh-wrap portion for encircling the thigh proximate the groin, wherein said wrap is constructed and arranged to define a line of folding proximate to and generally parallel with the groin line and to be free of constraint between portions of said abdomen- and thigh-wrap portions that pass posteriorly of the person that would otherwise prevent the person from bending between sitting and supine positions, and further including such a pressure-applying means wherein said pressure-applying means comprises first inflatable balloon means for disposition exclusively to the abdomen-side of the groin line beneath said abdomen-wrap portion and second inflatable balloon means for disposition exclusively to the thigh-side of the groin line beneath said thigh-wrap portion.

2. A wrap and pressure-applying means as set forth in claim 1 wherein said first and second balloon means comprise respective edges for disposition substantially parallel with the groin line, and means joining said edges to provide a line of folding between said first and second balloon means.

* * * * *